(12) United States Patent
Cryder et al.

(10) Patent No.: US 12,369,899 B2
(45) Date of Patent: *Jul. 29, 2025

(54) DEVICES AND SYSTEMS FOR SURGICAL RETRACTION

(71) Applicant: GLOBUS MEDICAL, INC., Audubon, PA (US)

(72) Inventors: Joel Cryder, Warrington, PA (US); Mark Weiman, Downingtown, PA (US)

(73) Assignee: Globus Medical Inc., Audubon, PA (US)

( * ) Notice: Subject to any disclaimer, the term of this patent is extended or adjusted under 35 U.S.C. 154(b) by 1168 days.

This patent is subject to a terminal disclaimer.

(21) Appl. No.: 17/206,511

(22) Filed: Mar. 19, 2021

(65) Prior Publication Data

US 2021/0204927 A1  Jul. 8, 2021

Related U.S. Application Data

(60) Continuation of application No. 16/364,438, filed on Mar. 26, 2019, now Pat. No. 10,980,528, which is a (Continued)

(51) Int. Cl.
*A61B 17/02* (2006.01)
*A61B 17/70* (2006.01)
(Continued)

(52) U.S. Cl.
CPC ........ *A61B 17/025* (2013.01); *A61B 17/0206* (2013.01); *A61B 17/7032* (2013.01); *A61B 17/708* (2013.01); *A61B 17/7082* (2013.01); *A61B 2017/00477* (2013.01); *A61B 2017/0256* (2013.01); *A61B 17/7035* (2013.01); *A61B 17/8605* (2013.01); *A61B 2090/037* (2016.02)

(58) Field of Classification Search
CPC . A61B 17/02; A61B 17/0206; A61B 17/0218; A61B 2017/0256; A61B 17/025
See application file for complete search history.

(56) References Cited

U.S. PATENT DOCUMENTS 5,549,608 A * 8/1996 Errico ................ A61B 17/7037
606/264
5,928,139 A * 7/1999 Koros ................ A61B 17/0206
600/245

(Continued)

FOREIGN PATENT DOCUMENTS

JP 2012527327 A 11/2012
JP 2013509982 A 3/2013
(Continued)

*Primary Examiner* — Lynnsy M Summitt

(57) ABSTRACT

Retractor blade assemblies, retractors, kits, and methods of using the same. The retractor blade assembly may include a retractor blade, a pedicle screw, and a screw mount that connects the pedicle screw to the retractor blade. The retractor blade may have a proximal end configured to engage a retractor body and a distal end configured to retract soft tissue. The pedicle screw may have a head portion removably connected to the distal end of the retractor blade and a shaft portion configured to engage the pedicle of a vertebra. The screw mount couples the pedicle screw to the retractor blade.

9 Claims, 27 Drawing Sheets

Related U.S. Application Data division of application No. 15/396,854, filed on Jan. 3, 2017, now Pat. No. 10,278,687, which is a continuation-in-part of application No. 14/828,695, filed on Aug. 18, 2015, now Pat. No. 9,700,293.

(51) Int. Cl.
- *A61B 17/00* (2006.01)
- *A61B 17/86* (2006.01)
- *A61B 90/00* (2016.01)

(56) References Cited

U.S. PATENT DOCUMENTS

| | | | | |
|---|---|---|---|---|
| 7,090,680 | B2* | 8/2006 | Bonati | A61B 17/8891 606/104 |
| 7,758,584 | B2* | 7/2010 | Bankoski | A61B 17/7079 606/104 |
| 7,819,801 | B2* | 10/2010 | Miles | A61B 1/32 600/210 |
| 7,922,658 | B2* | 4/2011 | Cohen | A61B 17/0206 600/210 |
| 8,043,343 | B2* | 10/2011 | Miller | A61B 17/7038 606/279 |
| 8,118,737 | B2* | 2/2012 | Perez-Cruet | A61B 17/025 600/206 |
| 8,357,184 | B2* | 1/2013 | Woolley | A61B 17/7076 606/279 |
| 8,535,318 | B2* | 9/2013 | Peterson | A61B 17/025 606/104 |
| 8,608,746 | B2* | 12/2013 | Kolb | A61B 17/7086 606/86 A |
| 8,636,655 | B1* | 1/2014 | Childs | A61B 17/0206 600/219 |
| 8,636,782 | B2* | 1/2014 | Biedermann | A61B 17/7037 606/279 |
| 8,834,485 | B2* | 9/2014 | Kave | A61B 17/7074 606/205 |
| 8,940,024 | B2* | 1/2015 | Biedermann | A61B 17/7037 606/307 |
| 8,974,381 | B1* | 3/2015 | Lovell | A61B 90/30 600/222 |
| 9,044,280 | B1* | 6/2015 | Arambula | A61B 5/389 |
| 9,101,413 | B2* | 8/2015 | Masson | A61B 17/025 |
| 9,216,016 | B2* | 12/2015 | Fiechter | A61B 17/0206 |
| 9,517,092 | B2* | 12/2016 | Biedermann | A61B 17/7076 |
| 9,572,560 | B2* | 2/2017 | Mast | A61B 17/025 |
| 9,597,095 | B2* | 3/2017 | Black | A61B 17/1703 |
| 9,622,795 | B2* | 4/2017 | Reitblat | A61B 17/708 |
| 9,795,370 | B2* | 10/2017 | O'Connell | A61B 17/0218 |
| 9,795,417 | B2* | 10/2017 | Beger | A61B 17/7035 |
| 9,808,281 | B2* | 11/2017 | Solitario, Jr. | A61B 17/3421 |
| 9,820,729 | B2* | 11/2017 | Miles | A61B 17/3421 |
| 9,888,948 | B2* | 2/2018 | Petit | A61B 17/7091 |
| 10,258,390 | B2* | 4/2019 | Biedermann | A61B 17/7076 |
| 10,278,786 | B2* | 5/2019 | Friedrich | A61B 17/0206 |
| 10,363,022 | B2* | 7/2019 | Serokosz | A61B 17/7077 |
| 10,499,896 | B2* | 12/2019 | Abidin | A61B 17/8891 |
| 11,166,707 | B2* | 11/2021 | Zakelj | A61B 17/7082 |
| 11,219,477 | B2* | 1/2022 | Biedermann | A61B 17/0206 |
| 11,413,028 | B2* | 8/2022 | Serokosz | A61B 17/025 |
| 2004/0068269 | A1* | 4/2004 | Bonati | A61B 17/8891 606/104 |
| 2005/0021040 | A1* | 1/2005 | Bertagnoli | A61B 17/708 606/90 |
| 2005/0065517 | A1* | 3/2005 | Chin | A61B 17/708 606/279 |
| 2005/0203532 | A1* | 9/2005 | Ferguson | A61B 17/025 606/90 |
| 2005/0203533 | A1* | 9/2005 | Ferguson | A61B 17/1757 606/90 |
| 2006/0074418 | A1* | 4/2006 | Jackson | A61B 17/7086 606/264 |
| 2006/0111712 | A1* | 5/2006 | Jackson | A61B 17/7086 606/264 |
| 2006/0200132 | A1* | 9/2006 | Chao | A61B 17/7077 606/279 |
| 2006/0247645 | A1* | 11/2006 | Wilcox | A61B 17/7077 606/86 R |
| 2006/0247649 | A1* | 11/2006 | Rezach | A61B 17/7077 606/90 |
| 2006/0293693 | A1* | 12/2006 | Farr | A61B 17/7085 606/104 |
| 2007/0106123 | A1* | 5/2007 | Gorek | A61B 17/1655 600/210 |
| 2007/0191856 | A1* | 8/2007 | Gil | A61B 17/7077 606/90 |
| 2007/0213715 | A1* | 9/2007 | Bridwell | A61B 17/025 606/264 |
| 2008/0021285 | A1* | 1/2008 | Drzyzga | A61B 17/708 600/215 |
| 2008/0140120 | A1* | 6/2008 | Hestad | A61B 17/7085 606/301 |
| 2009/0093684 | A1* | 4/2009 | Schorer | A61B 1/32 606/301 |
| 2009/0264895 | A1* | 10/2009 | Gasperut | A61B 17/864 606/104 |
| 2010/0286486 | A1* | 11/2010 | Parker | A61B 17/1757 600/235 |
| 2010/0331901 | A1* | 12/2010 | Lott | A61B 17/701 606/86 A |
| 2011/0004067 | A1* | 1/2011 | Marchek | A61B 17/02 600/214 |
| 2011/0034779 | A1* | 2/2011 | Louftus | A61B 17/7076 606/301 |
| 2011/0224497 | A1* | 9/2011 | Weiman | A61B 17/02 600/231 |
| 2012/0010471 | A1* | 1/2012 | Mire | A61B 17/025 600/210 |
| 2012/0046527 | A1* | 2/2012 | Cianfrani | A61B 17/0206 600/232 |
| 2012/0109208 | A1* | 5/2012 | Justis | A61B 17/8863 606/264 |
| 2012/0245431 | A1* | 9/2012 | Baudouin | A61B 17/0293 600/219 |
| 2012/0296171 | A1* | 11/2012 | Lovell | A61B 17/708 600/213 |
| 2012/0303062 | A1* | 11/2012 | Amstutz | A61B 17/7002 606/267 |
| 2014/0031874 | A1* | 1/2014 | Kucharzyk | A61B 17/025 606/279 |
| 2014/0121704 | A1* | 5/2014 | Solitario, Jr. | A61B 17/7083 606/86 A |
| 2015/0164495 | A1* | 6/2015 | Petit | A61B 17/0206 600/210 |
| 2015/0201987 | A1* | 7/2015 | Lemoine | A61B 17/8891 606/104 |
| 2015/0313585 | A1 | 11/2015 | Abidin et al. | |
| 2015/0351738 | A1* | 12/2015 | Perrow | A61B 17/0206 600/233 |
| 2016/0113685 | A1* | 4/2016 | Ishii | A61B 17/7037 606/266 |
| 2016/0113694 | A1* | 4/2016 | Rezach | A61B 17/7077 606/308 |
| 2016/0367295 | A1* | 12/2016 | Biedermann | A61B 17/7085 |
| 2017/0143323 | A1* | 5/2017 | Cryder | A61B 17/7032 |
| 2017/0164985 | A1* | 6/2017 | Reitblat | A61B 17/7074 |
| 2017/0196597 | A1* | 7/2017 | Corbin | A61B 17/7049 |
| 2017/0215856 | A1* | 8/2017 | Martinelli | A61B 5/742 |
| 2017/0224391 | A1* | 8/2017 | Biester | A61B 17/708 |
| 2018/0008253 | A1* | 1/2018 | Thommen | A61B 17/025 |
| 2023/0414259 | A1* | 12/2023 | Medeiros | A61B 90/57 |

FOREIGN PATENT DOCUMENTS

| | | |
|---|---|---|
| JP | 2014050714 A | 3/2014 |
| JP | 2014515646 A | 7/2014 |
| JP | 2014147684 A | 8/2014 |
| WO | 2011059491 A1 | 5/2011 |

(56) References Cited

FOREIGN PATENT DOCUMENTS

| WO | 2015116624 A1 | 8/2015 |
| WO | 2016025020 A2 | 2/2016 |
| WO | 2017031287 A1 | 2/2017 |

* cited by examiner

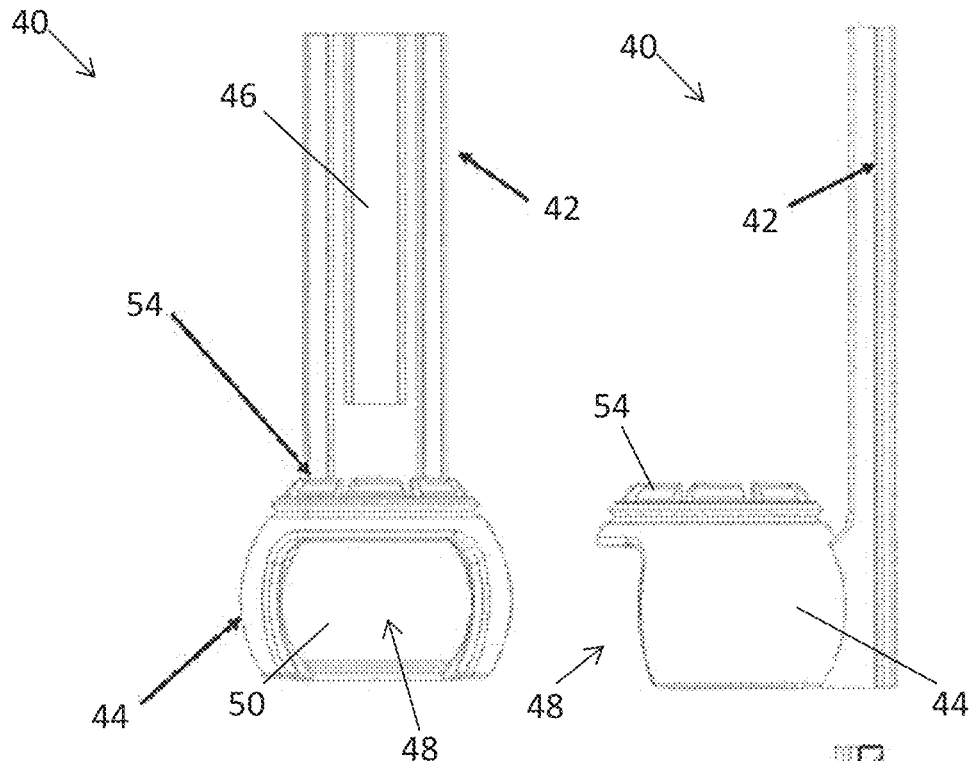
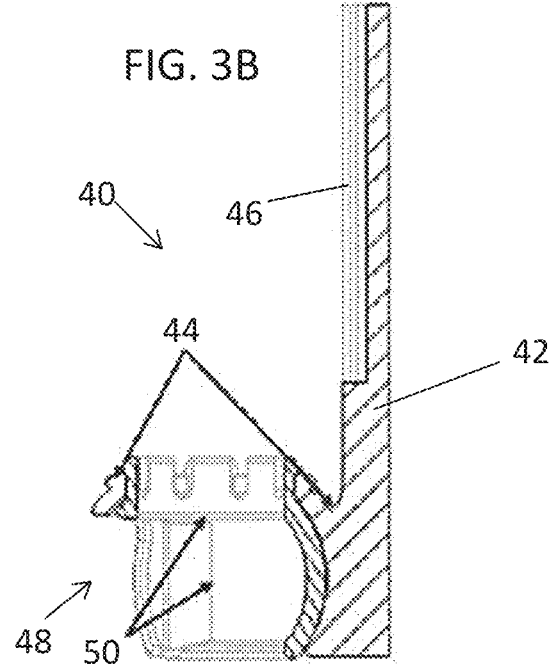
FIG. 3A   FIG. 3B
FIG. 3C

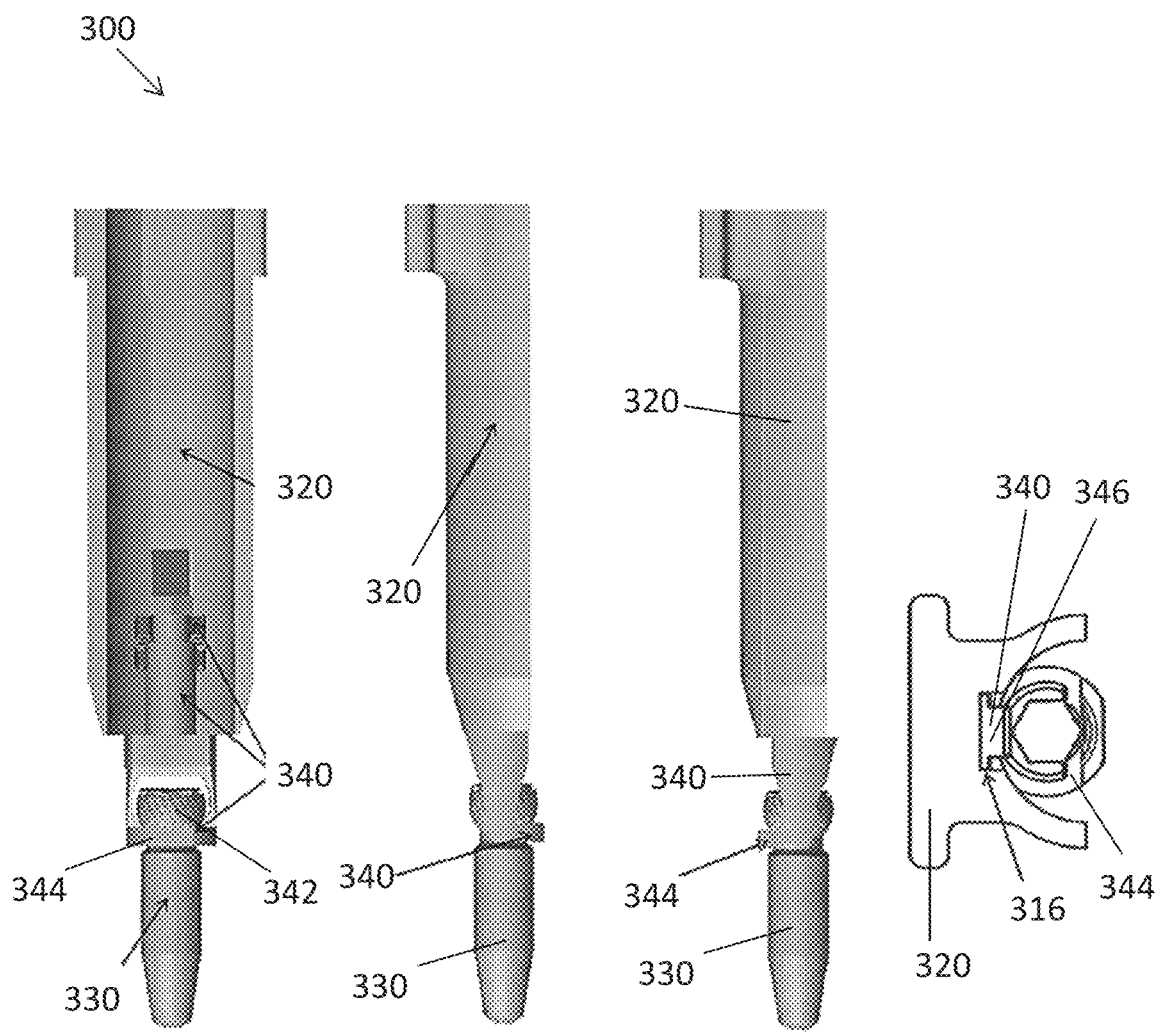

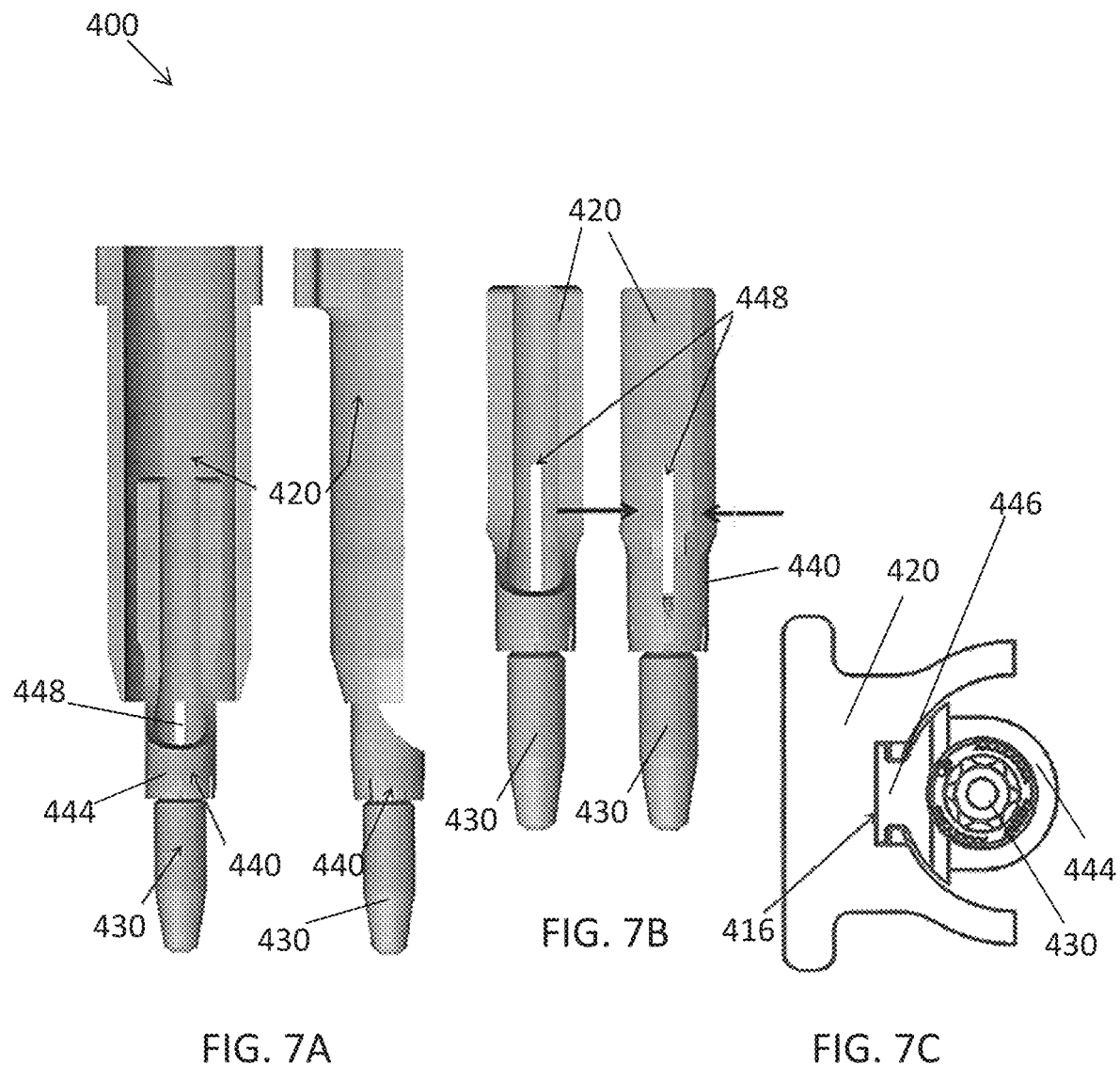

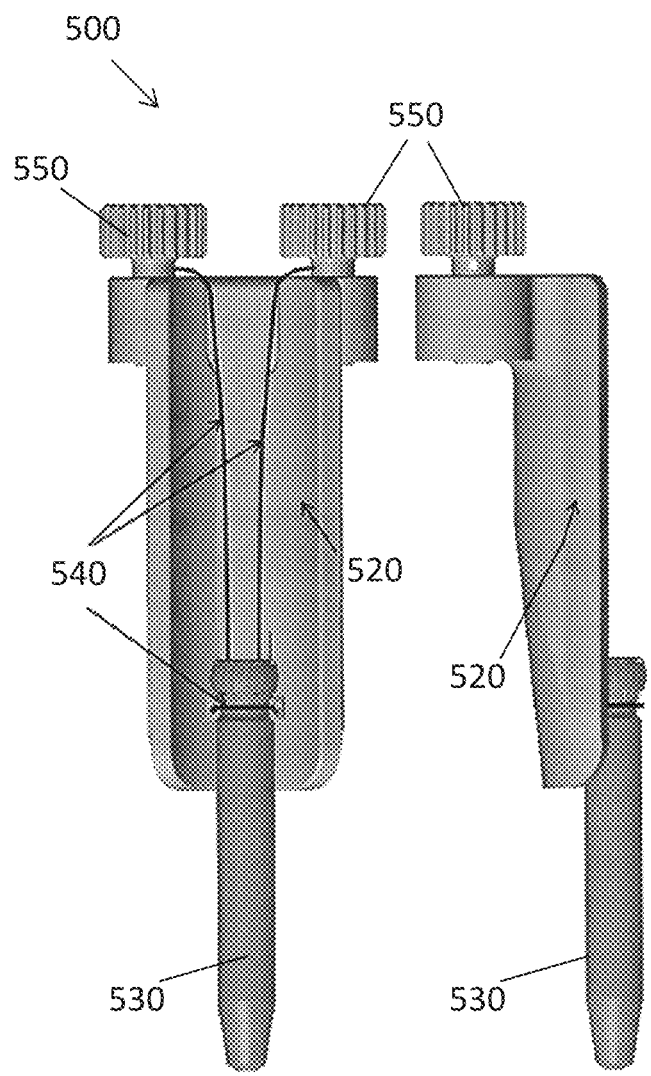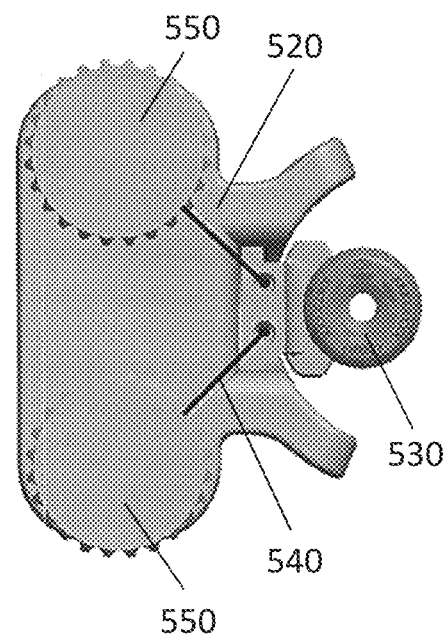
FIG. 8A  FIG. 8B  FIG. 8C

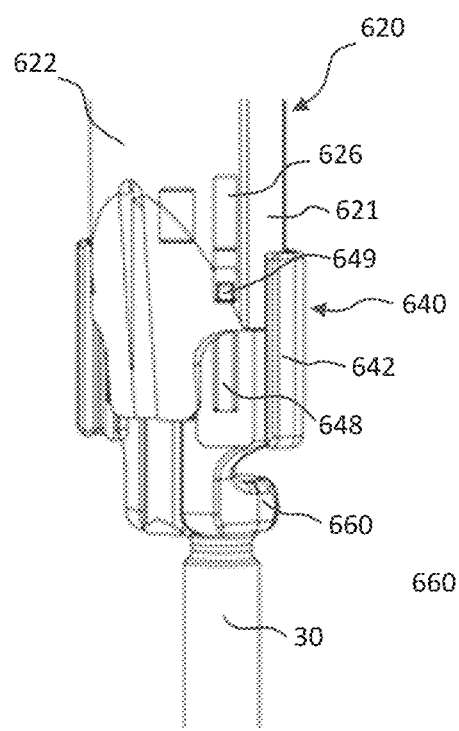
FIG. 10I
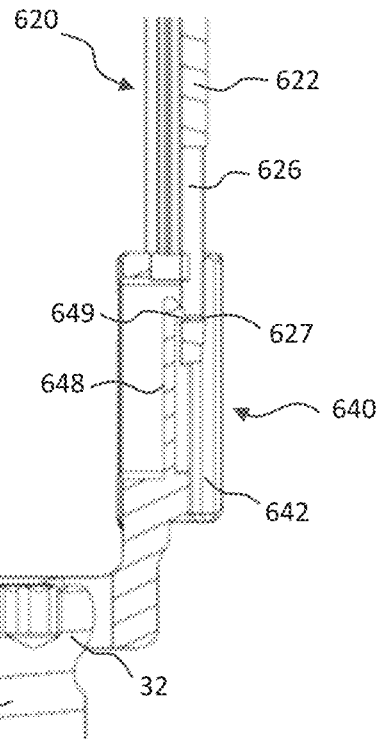
FIG. 10J
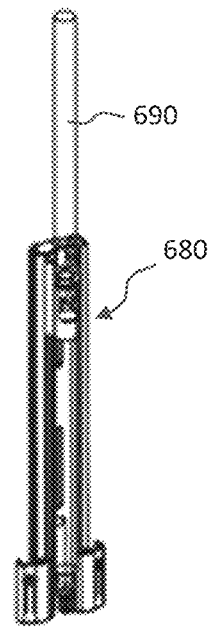
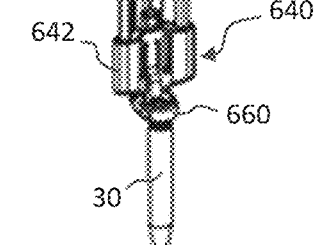
FIG. 10K

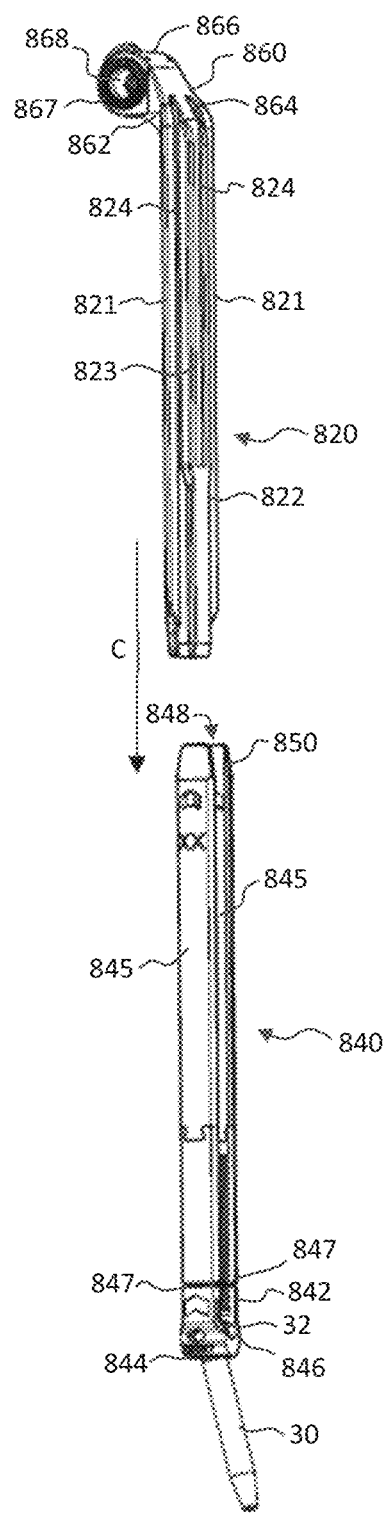
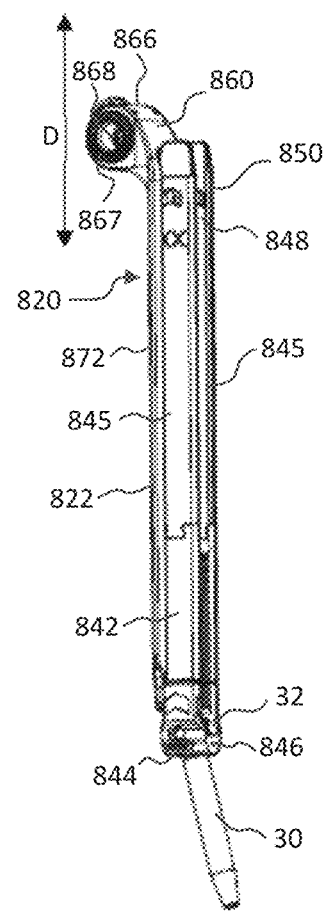
FIG. 12A
FIG. 12B

DEVICES AND SYSTEMS FOR SURGICAL RETRACTION

CROSS-REFERENCE TO RELATED APPLICATION

This application is a continuation of U.S. patent application Ser. No. 16/364,438 filed on Mar. 26, 2019, which is a divisional of U.S. application Ser. No. 15/396,854, which is a continuation-in-part of U.S. application Ser. No. 14/828,695, filed on Aug. 18, 2015, now U.S. Pat. No. 9,700,293, the contents of which are incorporated herein by reference in their entities for all purposes.

FIELD OF THE INVENTION

The present disclosure generally relates to devices and systems for performing pedicle-based surgical retraction and/or distraction and methods of use thereof.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. Often, these irregularities are treated through a surgical procedure that may include, for example, immobilizing a portion of the spine. These treatments may involve, for example, replacing a damaged disc with an intervertebral implant and/or securing the adjacent vertebrae, for example, with a combination of screws and rods. For correction of a collapsed disc causing impingement of one or more nerve roots, for example, the disc space may be restored back to or near its original height and the collapsed disc may be replaced with a device and/or bone graft material.

In order to perform these procedures, a surgical opening is created, and a device such as a retractor may be used to enlarge the opening and facilitate access to the surgical site. The retractor may typically include one or more blades that can be adjusted to establish, provide, and/or maintain an appropriate opening that minimizes trauma to surrounding tissue. A distractor may also be used to distract the disc space, for example, by placing a portion of the distractor between vertebral bodies or by using adjacent level pedicle screws.

By using a pedicle-based retraction system, the retractor can perform the functions of both a retractor and a distractor. For example, the blades may provide for soft tissue retraction, and the pedicle screws may be configured to simultaneously facilitate distraction of the disc space. There is a need, however, for improved retractors which provide pedicle-based distraction and soft tissue retraction. For example, pedicle-based retractors require a secure connection between the blade and the pedicle screw. It is also desirable to have a mechanism to attach the blades to the screws after the screws have already been affixed to bone. Preferably, there is a minimal amount of tissue disruption when connecting the blades to the screws intra-operatively.

SUMMARY OF THE INVENTION

To meet this and other needs, devices, systems, and methods for performing pedicle-based surgical retraction are provided. In particular, the pedicle-based retractors are provided with specially designed connections between the pedicle screw and blade, which create a secure reversible connection between the pedicle screw and the retractor blade. After the screw is implanted in the bone, the blade may be attached to the screw in a manner to minimize the amount of tissue disruption at the surgical site.

According to one embodiment, a retractor blade assembly includes a retractor blade, a screw, and a shim which connects the screw to the retractor blade. The retractor blade may have a proximal end configured to engage a retractor body and a distal end configured to retract soft tissue. The screw may have a head portion removably connectable to the distal end of the retractor blade and a shaft portion configured to engage bone. The shim may have an extension portion configured to engage the retractor blade and a connection portion configured to receive at least a portion of the screw. The connection portion may be movable from an unlocked position to a locked position for retaining the screw within the shim.

According to another embodiment, a retractor assembly includes a retractor body, at least one retractor blade, at least one pedicle screw, and at least one shim that connects the pedicle screw to the retractor blade. The retractor blade may have a proximal end configured to engage the retractor body and a distal end configured to retract soft tissue. The pedicle screw may have a head portion removably connectable to the distal end of the retractor blade and a shaft portion configured to engage bone. The shim may have an extension portion, an outer spherical portion, and an inner spherical portion rotatably received within the outer spherical portion. The extension portion may be configured to engage the retractor blade and the inner spherical portion may be configured to receive the head portion of the pedicle screw. The inner spherical portion rotates from an unlocked position to a locked position for retaining the head portion of the pedicle screw within the shim.

The retractor blade assembly and/or the retractor assembly may include one or more of the following attributes: the extension portion may include at least one rail configured to slidably engage at least one corresponding rail on the retractor blade; the extension portion may include at least one edge configured to surround one or both end portions of the retractor blade; the retractor blade may include a generally curved inner portion having one or more grooves defined along at least a portion of the at least one retractor blade, the one or more grooves configured to slidably engage one or more corresponding tongues of the extension portion of the at least one shim; the shim may include an elongated slot extending longitudinally along a length of the shim; the connection portion may be configured to rotate relative to the retractor blade; the connection portion may include at least a partial ring configured to at least partially surround the head portion of the screw; a top portion of the inner spherical portion may extend through an opening in the outer spherical portion, and the top portion may be configured to be engaged by a driver in order to rotate the inner spherical portion from the unlocked position to the locked position; the screw may be side-loaded into the shim; the outer spherical portion and the inner spherical portion may each include an opening that, when aligned, allow the pedicle screw to be side-loaded into the shim; the pedicle screw may be configured to polyaxially rotate in the shim; one or more locks may be positioned along one or both outer edges of the retractor blade to prevent the shim from sliding off the retractor blade; and the driver may include at least one track configured to engage the at least one rail on the extension portion of the shim.

According to yet another embodiment, a method of retracting and distracting a disc space between first and second vertebrae may include: (a) connecting a driver to a first shim; (b) attaching a first pedicle screw to the first shim by side loading the first pedicle screw into the first shim and locking the first pedicle screw to the first shim; (c) attaching the first pedicle screw to a pedicle of the first vertebra; (d) sliding a first retractor blade having a proximal portion and a distal portion down the driver and onto the first shim such that the distal portion of the first retractor blade connects to the first shim; (e) removing the driver; and (f) connecting a retractor body to the proximal portion of the first retractor blade. In addition, the method may optionally include: (g) connecting the driver to a second shim; (h) attaching a second pedicle screw to the second shim by side loading the second pedicle screw into the second shim and locking the second pedicle screw to the second shim; (i) attaching the second pedicle screw to a pedicle of the second vertebra; (j) sliding a second retractor blade having a proximal portion and a distal portion down the driver and onto the second shim such that the distal portion of the second retractor blade connects to the second shim; (k) removing the driver; (l) connecting the retractor body to the proximal portion of the second retractor blade; and (m) retracting and distracting the disc space using the first and second retractor blades and the first and second pedicle screws, respectively.

According to yet another embodiment, a kit may include a plurality shims, blades, and/or screws of different sizes and different configurations. The kit may further include one or more retractor bodies and attachment mechanisms, such as surgical arms, table arms, or the like. In addition, the kit may include one or more devices suitable for installing and/or removing the retractor blade assemblies described herein, such as insertion devices or drivers; one or more removal devices or drivers; and other tools and devices, which may be suitable for surgery.

According to another embodiment, a retractor blade assembly includes a pedicle screw, a retractor blade and a screw mount. The pedicle screw has a head portion and a shaft portion configured to engage bone. The retractor blade has a proximal end and a distal end configured to retract soft tissue. The screw mount has an extension portion defining at least one blade mounting assembly and a head portion defining a screw head receiving chamber. The chamber is defined by a concave interior wall of the head portion and a moveable retaining member extending from the extension portion with a free end of the retaining member extending within the head portion and defining a concave surface opposed to the concave interior wall.

According to yet another embodiment, a retractor blade assembly includes a pedicle screw, a tulip screw mount and a retractor blade. The pedicle screw has a head portion and a shaft portion configured to engage bone. The tulip screw mount includes a tulip with a closed end defining a screw head seat and extension legs extending proximally from the tulip with a slot extending therebetween. The retractor blade has a body extending between a proximal end and a distal end configured to retract soft tissue, the retractor blade body defining a rail configured to be received in the screw mount slot to retain the retractor blade on the tulip screw mount.

According to another embodiment, a method of connecting a retractor blade to a pedicle is provided. The method includes connecting a driver to a screw mount. The screw mount includes an extension portion and a head portion, the head portion having a concave internal wall and the extension portion including a moveable retaining member with a free end that extends into the head portion such that a concave surface of the retaining member is opposed to the concave internal wall to define a screw head chamber. The method further includes positioning the head of a pedicle screw within the chamber and moving a locking mechanism to a locking position wherein a portion of the locking mechanism engages the retaining member and prevents the retaining member from moving radially outwardly. The pedicle screw is attached to a pedicle of a vertebra and a retractor blade, having a proximal portion and a distal portion, is slid down the driver and onto the screw mount such that the distal portion of the retractor blade connects to the screw mount.

BRIEF DESCRIPTION OF THE DRAWINGS

The present embodiments will become more fully understood from the detailed description and the accompanying drawings, wherein:

FIGS. 6A-6D depict an alternative attachment mechanism between a pedicle screw and a retractor blade;

FIGS. 7A-7C illustrate yet another attachment mechanism between a pedicle screw and retractor blade;

FIGS. 8A-8C show attachment of a retractor blade member to a pedicle screw according to another embodiment;

FIGS. 10A-10K show attachment of a retractor blade member to a pedicle screw according to another embodiment;

FIGS. 12A-12D illustrate components and a series of steps, which may be used to install a pedicle screw in bone and mount a retractor blade thereto in accordance with another embodiment.

DETAILED DESCRIPTION

Figure 1:
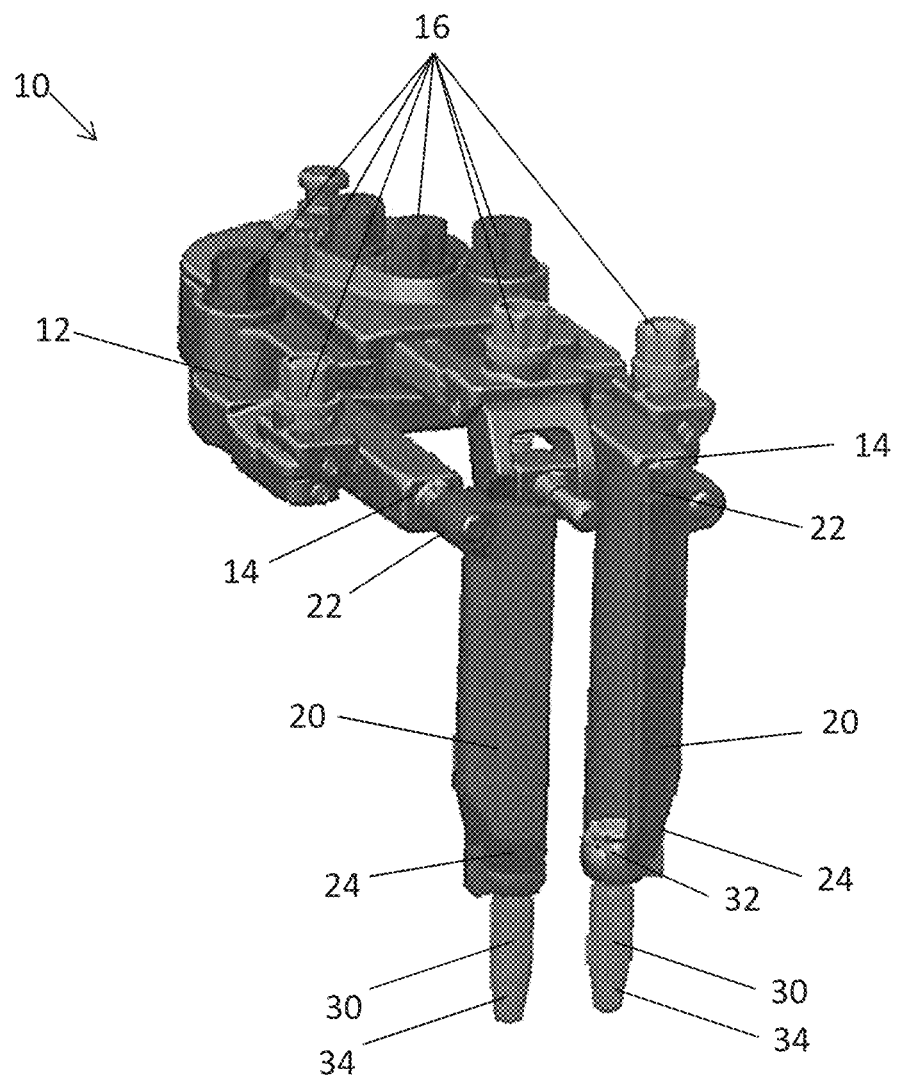
FIG. 1 illustrates a perspective view of a retractor assembly according to one embodiment.

Embodiments of the disclosure are generally directed to devices, systems, kits, and methods for retraction and/or distraction using a pedicle-based retraction system. Specifically, the pedicle-based retractors include secure and reversible connections between the pedicle screw and retractor blade. The retractor blade may be attached to the screw before or after the screw has been implanted in the bone. When attached intra-operatively, the attachment mechanism may minimize the amount of tissue disruption at the surgical site.

In a spinal fusion procedure, a damaged spinal disc may be removed and replaced with an intervertebral implant (e.g., a cage, spacer, vertebral body replacement, bone graft material, or other prosthetic). The adjacent vertebrae may be stabilized, for example, with a combination of screws and rods. The operation may be performed in an open procedure, semi-open procedure, percutaneous, or in a minimally invasive surgical (MIS) procedure. As part of the procedure, a retractor may be used to establish, enlarge, manipulate, and/or maintain a surgical opening, thereby facilitating the passage of the various implant devices and related tools. In some instances, different retractors may be used for different surgical approaches (e.g., anterior, posterior, transforaminal, lateral), due to the varying anatomical features unique to each approach. The retractor blades may be used to hold back soft tissue and muscle, and precise angling of the retractor's blades may depend at least in part on various factors, including the particular patient's anatomy and surgeon's preference.

Overall, retractor systems disclosed herein may advantageously provide a screw-based retraction and distraction, resulting in more precise tissue retraction and distraction of adjacent bones. In particular, a pedicle-based retraction system may include one or more retractor blades temporarily affixed to one or more pedicle screws each configured to engage a pedicle of a vertebra. Once attached to a retractor body, the retractor blades and attached pedicles may retract soft tissue and/or muscle and distract the disc space. Although described herein with regards to specific pedicle-based blade designs, those skilled in the art may appreciate that the blades described herein may be used in any suitable retractor design.

As used herein, the terms "proximal" and "distal" are utilized generally with reference to a user (e.g., a surgeon). When used with reference to the retractor assembly, described further herein, the terms "lateral" and "medial" refer generally to the ends and the middle position, respectively. For example, a retractor arm traveling in a lateral direction may be traveling from a middle portion outwardly, and a retractor arm traveling in a medial direction may be traveling from an end portion towards the middle. These and other directional terms such as "top" and "bottom" and the like may be used herein for descriptive purposes and do not limit the orientation(s) in which the devices may be used.

Some embodiments may include a two-bladed retractor. The retraction may be controlled medially and laterally, for example. Each blade may also have a towing or pivoting capability. Although a two blade design is exemplified, it is understood that the retractor may encompass three or more blades, four or more blades, or the like in order to provide retraction in the medial, lateral, cephalad, caudal, or other orientations as may be desired.

The retractor system may include a variety of sub-components dimensioned to allow for retraction of soft tissue and/or muscle in order to establish an operative corridor through a patient's skin to a surgical target site as well as a screw-based component to allow for distraction of adjacent bones. By way of example, the surgical target site may be an intervertebral disc space situated between two adjacent vertebrae. Although particularly suited for use in a transforaminal lumbar interbody fusion (TLIF), it will be readily appreciated by those skilled in the art that the retractor system may be employed in any number of suitable orthopedic approaches and procedures, including but not limited to, anterior, posterior, lateral, anterolateral, or posterolateral approaches to the lumbar spine, cervical spine, or thoracic spine, as well as any non-spine application, such as treatment of bone fractures and the like.

Turning now to the drawing, where like reference numerals refer to like elements, FIG. 1 illustrates a retractor system 10. The retractor system 10 includes a frame or base 12 that is attachable to an arm and/or supporting structure (not shown). For example, the base 12 may be directly or indirectly attachable to a table, a rack, a cart, or the like. In one embodiment, the base 12 is configured to be attached to a surgical arm, such as a universal arm, which includes enough joints to provide a desired number of degrees of freedom to easily adjust the base 12 over an incision in a patient. Preferably, the base 12 is configured to be positioned in a substantially stationary position over the surgical access site.

Broadly, the base 12 provides a scaffold to hold the various components together and one or more mechanisms for operating the retraction and/or distraction. In particular, the base 12 provides a mechanism to expand the operative corridor by moving the retractor blades 20 toward or away from one another. The base 12 may include one or more arms or posts 14 configured to receive or attach to one or more blades 20 thereto. Each post 14 is configured to enable the retractor blades 20 to retract nearby soft tissue and/or distract a bone segment. The base 12 includes one or more knobs 16 configured to operate the retractor 10. For example, the knobs 16 may provide for movement of posts 14, thereby providing for movement of the blades 20. Each of the respective knobs 16 may provide for independent movement of each respective blade 20 including lateral movement, medial movement, pivoting or towing or the blades 20, or the like as will be recognized by one of ordinary skill in the art. Although one type of retractor 10 is exemplified herein, it is understood that any suitable retractors known in the art may be used. Further detail of such devices may be found, for example, in U.S. Pat. Nos. 8,852,090; 8,932,215; 8,968,363; and 8,992,425, which are incorporated by reference herein in their entireties for all purposes.

One or more blades 20 are removably coupled to the base 10. The position of each retractor blade 20 can be changed independent from the other retractor blades 20, which allows a great amount of flexibility to the surgeon to explore an operating field. Furthermore, the position of each retractor blade 20 can be changed without changing the position of the base 10. Thus, the base 10 may remain in a substantially stationary and fixed position over the incision. In this regard, a change in the operating field can be obtained by changing the position of the blades 20.

In general, each retractor blade 20 has a first, proximal end portion 22 configured to engage with the base 12, for example, having an opening to receive post 14 and a second, distal end portion 24 configured to connect with a screw member 30. Each blade also includes an inner face, an outer face, and a longitudinal axis running the length of the blade 20 from the proximal end 22 to the opposite distal end 24. Different blade geometries may be used based on the patient anatomy and surgeon preference. For example, the blades 20 may be provided with a convexity at the proximal end 22 to cup under tissue and muscle to prevent the blades 20 and retractor from floating upward. In one embodiment, the retractor blades 20 have a curved or partial cylindrical shape, such that when blades 20 are aligned adjacent one another, a cylinder, channel, cannula, or the like is created therebetween. The size of the retractor blades 20 may dependent on the type of surgical procedure. The type, size, and shape of the surgical retractor blades 20 can be mixed together as well as changed or renewed during a surgical procedure.

The screw member 30 is configured to be removably attached to the retractor blade 20 as described in the various embodiment provided herein. The screw member 30 may include a head portion 32 (e.g., an enlarged head 32) at a proximal end configured to engage the retractor blade 20 and a shank or bone engagement portion 34 configured to engage bone, for example, having a taper at a distal end. The screw member 30 may be centrally cannulated along a longitudinal length from the proximal end to the distal end of the screw member 30, for example, such that the screw member 30 may be guided over a k-wire or the like. The screw member 30 may be in the form of a pedicle screw 30 having a threaded portion configured to engage the pedicle in a vertebral body. The head portion 32 may also be threaded or non-threaded. The pedicle screw 30 may be configured to provide uni-planar, bi-planar, or poly-axial orientation of the shank, for example. In the alternative, the screw member 30 may include any fixation members, such as nails, spikes, shims, or the like, which are known in the art.

With reference on FIGS. 2A-2D, a system and method for attaching a pedicle screw member 30 to a blade 20 is provided. In particular, a shim or screw mount 40 connects the pedicle screw member 30 to the blade 20. The shim or screw mount 40 includes an extension portion 42 and a head portion 44. The extension portion 42 may include a track 46, for example, in the form of one or more recesses and/or protrusions extending along a longitudinal length of the extension portion 42. The track 46 is configured to slidably engage and mate with a corresponding track portion 62 on a driver 60. The head portion 44 of the screw mount 40 may be sized and configured to receive the head 32 from the screw member 30. In particular, the head portion 44 may define an opening or aperture 48 configured to allow for side-loading of the screw member 30. The head portion 44 may house an internal sphere 50 within. The internal sphere 50 may be sized and configured to rotationally reside within the head portion 44 of the screw mount 40. The internal sphere 50 may have an opening or aperture corresponding to aperture 48 in the head portion 44, when in an unlocked position, such that the screw member 30 may be side loaded into the screw mount 40. The internal sphere 50 may be rotated by driver 60 such that the aperture 48 of the head portion 44 is substantially blocked, thereby locking the screw member 30 within the head portion 44 of the screw mount 40 in a locked position.

The driver 60 may include a distal portion configured to engage the screw mount 40 and a proximal portion configured to engage a handle (not shown) or other instrumentation to be manipulated by a user (e.g., a surgeon). For example, a quick connect handle may be attached to the driver 60. The driver 60 may include an elongated outer shaft 66 having an inner shaft 68 received longitudinally therethrough. The inner shaft 68 may also be cannulated along its length, for example, to be guided by a k-wire or the like. The inner shaft 68 may be configured to rotate with respect to the outer shaft 66. The inner shaft 68 may terminate at a distal tip 64. The distal tip 64 may have a hexalobular portion, for example, which engages with a portion of the screw mount 40. The distal tip 64 may be of any suitable shape and configuration including, but not limited to, round, triangular, squared, polygonal, star, torx, irregular, uniform, non-uniform, offset, staggered and/or tapered. The outer shaft 66 may also include a track portion 62 extending longitudinally along a length of the driver 60. The track portion 62 may be in the form of one or more extensions or recesses configured to mate with a corresponding track 46 on the screw mount 40.

Figure 2A:
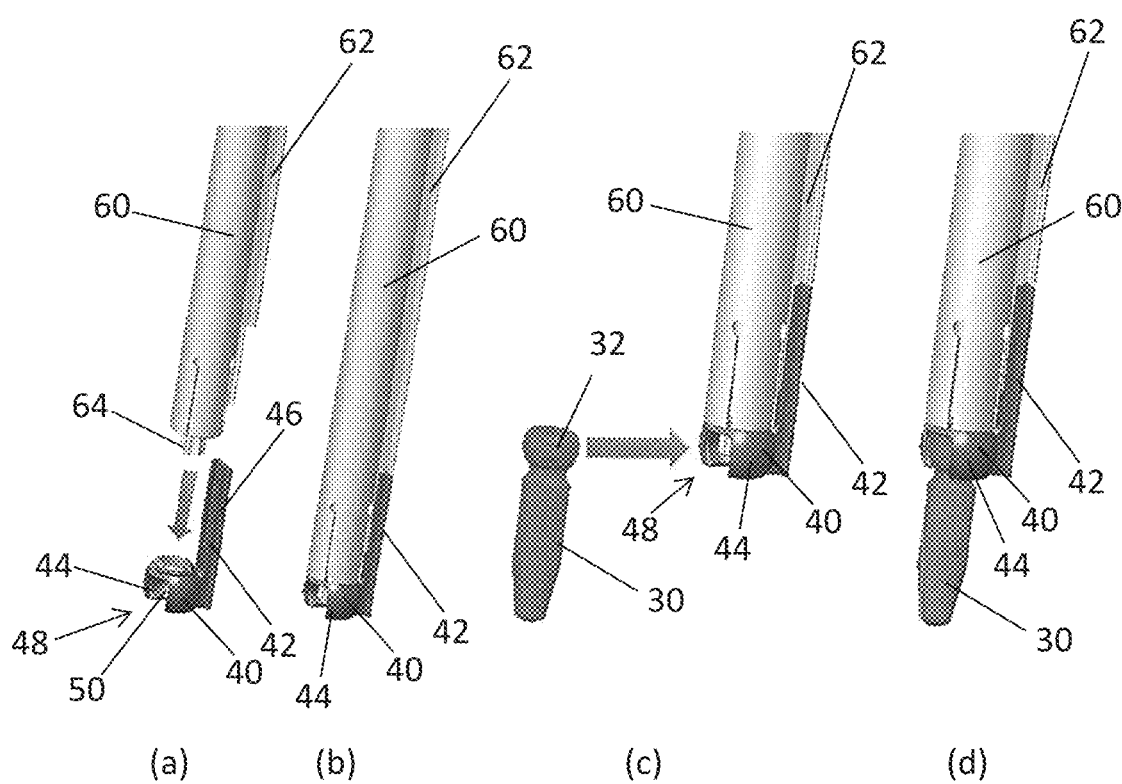
FIGS. 2A-2D illustrate the components and a series of steps, which may be used to install a pedicle screw in bone and mount a retractor blade thereto intra-operatively.

A series of steps, which may be used to install the pedicle screw 30 in bone and mount a retractor blade 20 thereto is further described. Any of these steps may be performed before or during the operation in any suitable order. The screw mounts 40 may be available as a kit or set, for example, in a caddy sitting upright (not shown), such that a user can use driver 60 to select a screw mount 40. With reference on FIG. 2A, shown in step (a), the driver 60 may be pressed downward onto the screw mount 40. In particular, the distal tip 64 of the driver 60 may include an extension configured to engage a corresponding recess in the top of the head portion 44 of the screw mount 40 and/or a recess in the head 32 of the screw member 30, for example, via a press-fit connection. In addition, the track portion 62 on the driver 60 may slidably engage the track 46 on the extension portion 42 of the screw mount 40. The corresponding and intermeshing tracks 46, 62 and press-fit connection of the tip 64 with head portion 44 may provide for visual, audible, and/or tactile feel when the driver 60 snaps onto the screw mount 40. The fully seated screw mount 40 on driver 60 is shown in step (b). After verifying the connection, a thumb knob (not shown) on the driver 60 can be utilized to make sure that the internal sphere 50 of the screw mount 40 is in the unlocked position (e.g., with apertures aligned to allow for side loading of the screw member 30).

As shown in step (c), the screw member 30 may be side-loaded into the screw mount 40. The hexalobular portion of the inner shaft 68 of the driver 60 may be pulled back and the screw head 32 inserted into the head portion 44 of the screw mount 40 from the side. The resulting construct is shown in step (d) with the screw member 30 received in screw mount 40 and attached to driver 60. The hexalobular portion of the driver 60 may then be pushed forward and engaged with the screw 30 (not visible).

Figure 2B:
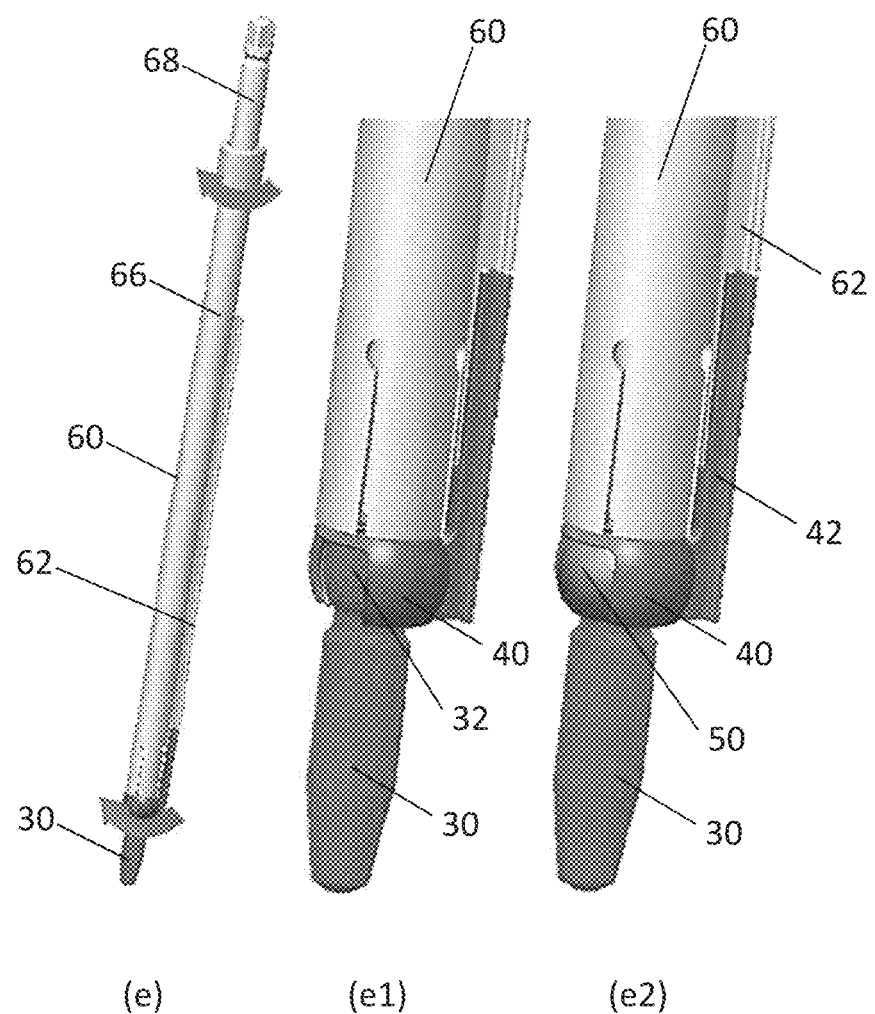

Turning now to FIG. 2B, as shown in step (e), the internal sphere 50 in the head portion 44 of the screw mount 40 may be rotated into the locked position. For example, a driver thumb knob may be rotated, for example, 180 degrees, to turn the internal sphere 50 to the locked position. A close up view of the screw mount 40 in the unlocked positioned is shown in (e1) and (e2) shows a close up view of the screw mount 40 in the locked position. A solid stop (not shown) may also be present to ensure that the internal sphere 50 remains in the locked position.

At the surgical site, a Jamshidi needle and k-wire may be placed into the pedicle. A series of cannulas may be inserted over the k-wire to dilate the tissue and obtain the blade length. The cannulas may then be removed, leaving the k-wire in place. The driver assembly, including the screw member 30 and screw mount 40 connected to the driver 60, may pass over the k-wire and the screw member 30 may be inserted into the pedicle (e.g., threaded into the pedicle).

Figure 2C:
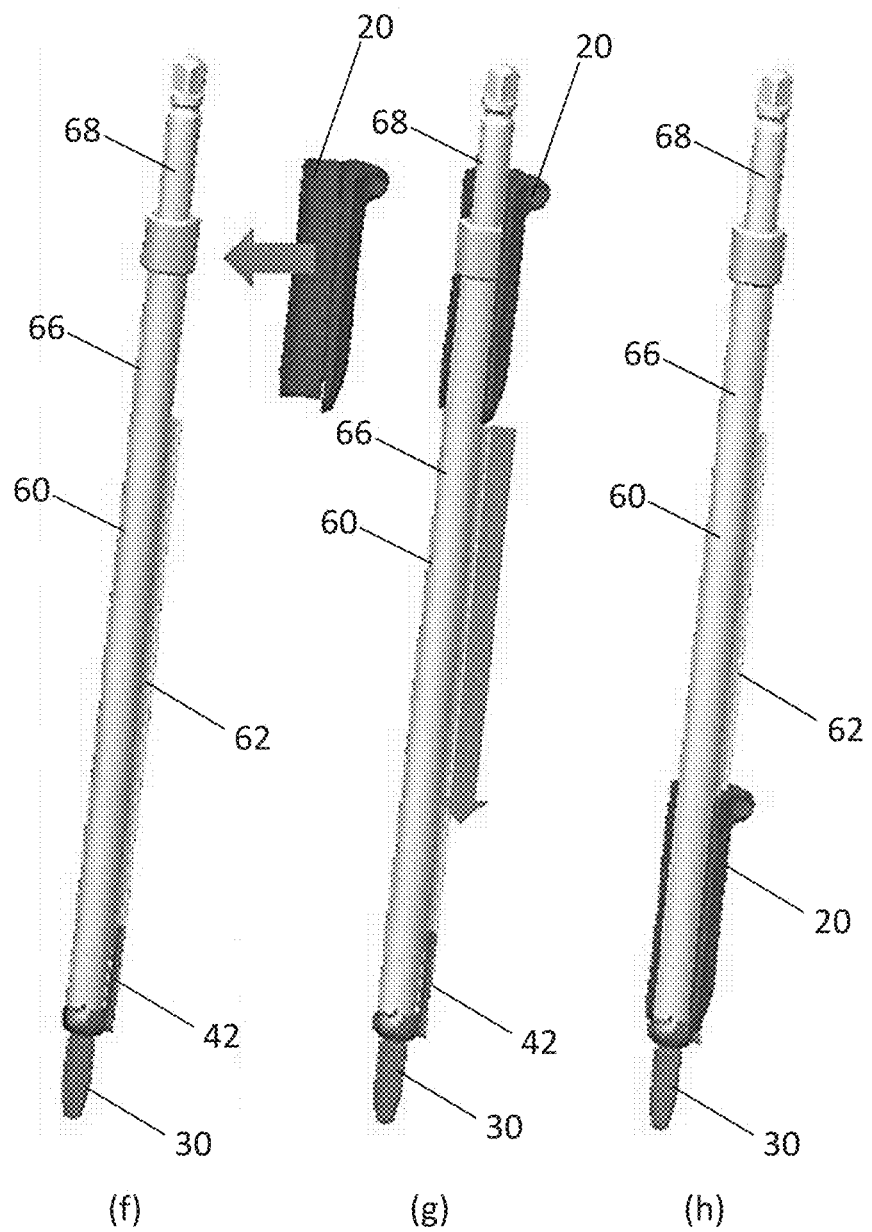

Turning now to FIG. 2C, prior to disconnecting the driver 60 from the screw mount 40, as shown in steps (f) and (g), the blade 20 may be engaged with the driver 60. As shown in step (h), the blade 20 may be slid down the side of the driver 60 and onto the screw mount 40. In particular, the blade 20 may also include a track configured to engage with the track 62 on the outer shaft 66 of the driver and connect with an outer portion of the extension portion 42 of the screw mount 40.

Figure 2D:
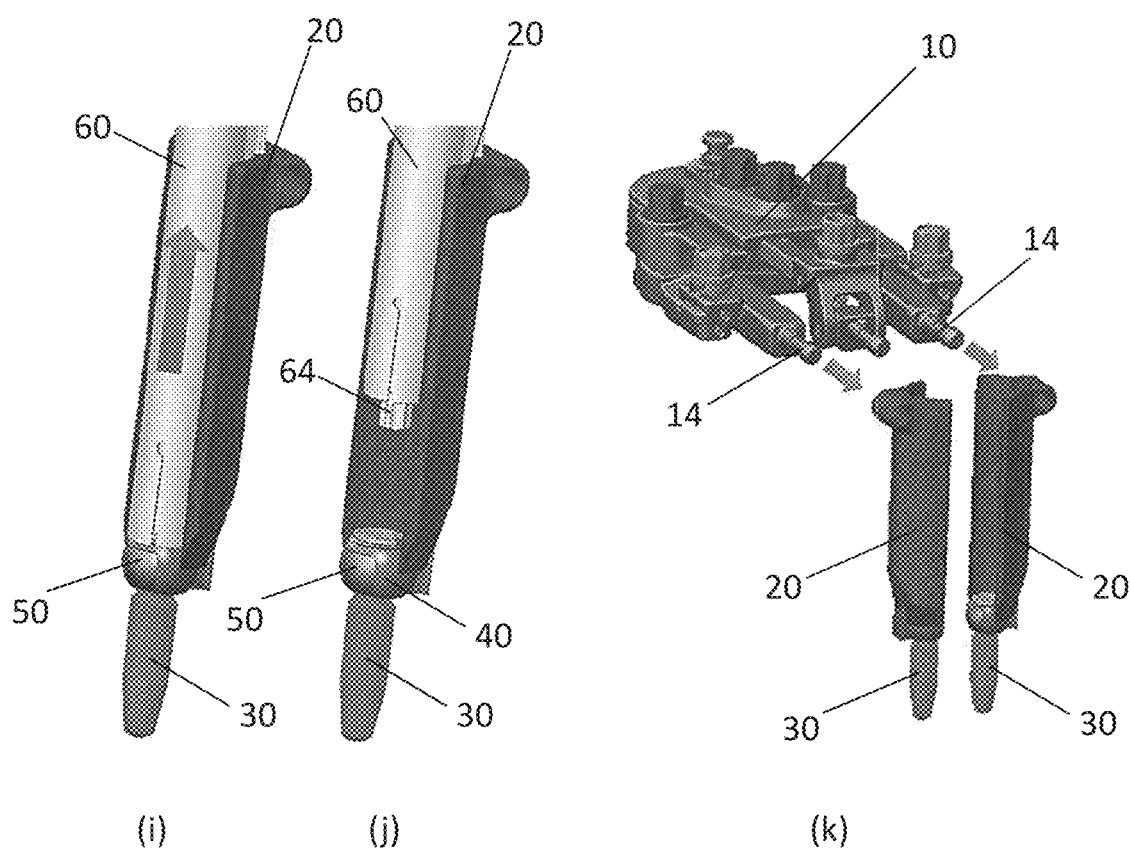

As best seen in FIG. 2D, in steps (i) and (j), once the blade 20 has been connected with the screw mount 40, the driver 60 can be removed. The series of driver assembly, screw insertion, blade insertion and driver removal may be repeated at the other pedicle sites as many times as necessary for the operation. Once the screws 30, screw mounts 40, and blades 20 are in place, as shown in step (k), the retractor body 10 can be attached to the blades 20, for example, from a side approach. As shown, the posts 14 can be positioned within openings in the blades 20. The blades 20, including the screw mounts 40 and screws 30, and the vertebral bodies attached thereto can now be manipulated by the retractor 10. For multi-level constructs, the retractor base 10 can be removed from the blades 20 and the retractor 10 reattached to adjacent blades 20. If necessary, the blades 20 and/or screw mount 40 may be rotated about the pedicle screw member 30 before the retractor 10 is reattached to adjacent blades 20.

After the interbody work has been completed, the same or a separate driver 60 may be introduced to turn the internal sphere 50 into the unlocked position. The retractor blades 20 can be retracted out further, thereby separating the screw member 30 from the screw mounts 40. The pedicle screws 30 can remain in the pedicles and can be used for a resulting fusion procedure (e.g., combined with rods). By moving the retractor blades 20 outward, this will allow enough space for screw tulips to be introduced and connected to the screw members 30. After rods and locking caps have been introduced, the retractor 10, blades 20, and screw mounts 40 may be removed, for example, at the same time.

Figures 3D, 3E:
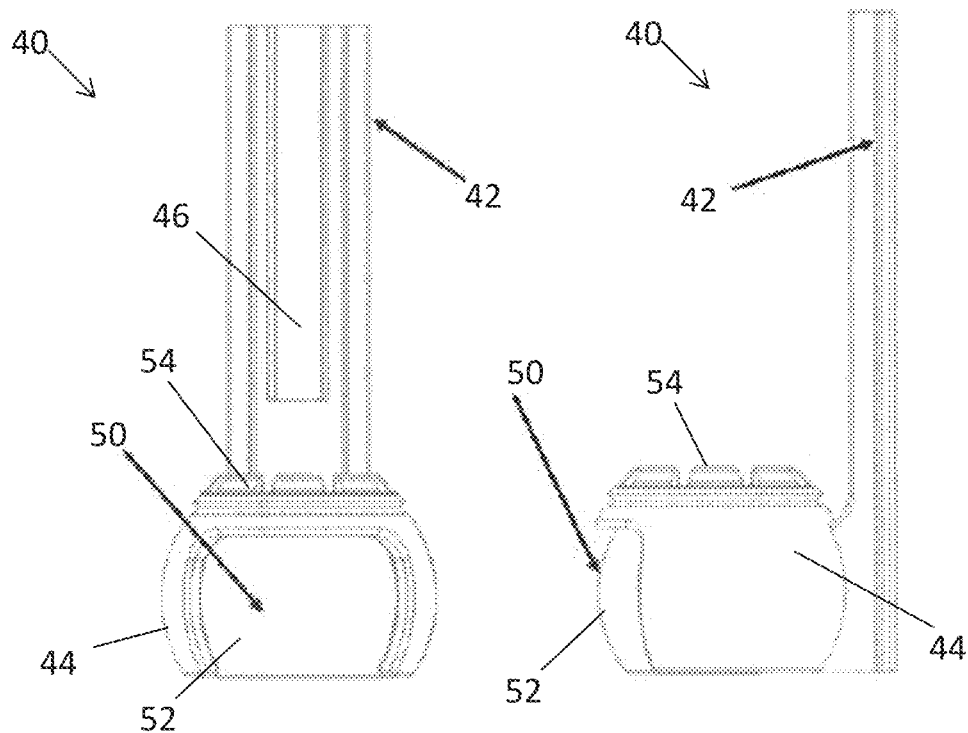
FIGS. 3A-3P provide additional detail of shims or screw mounts suitable for use in attaching a pedicle screw to the retractor blade.
Figure 3F:
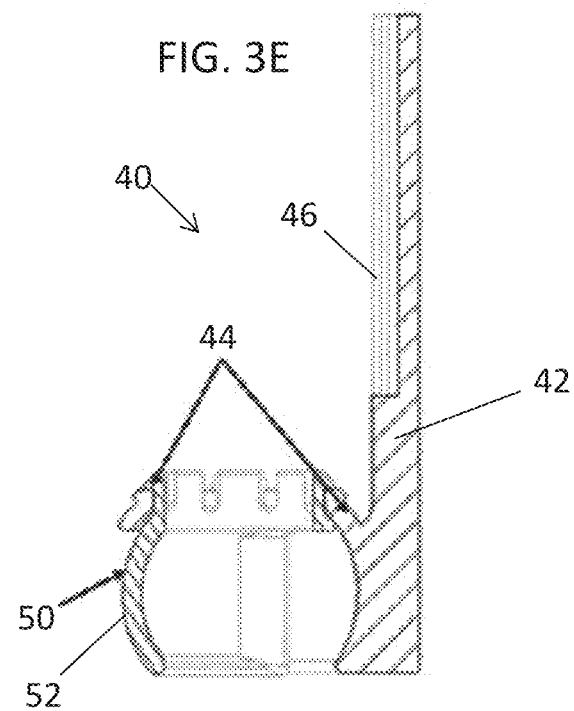
Figure 3G:
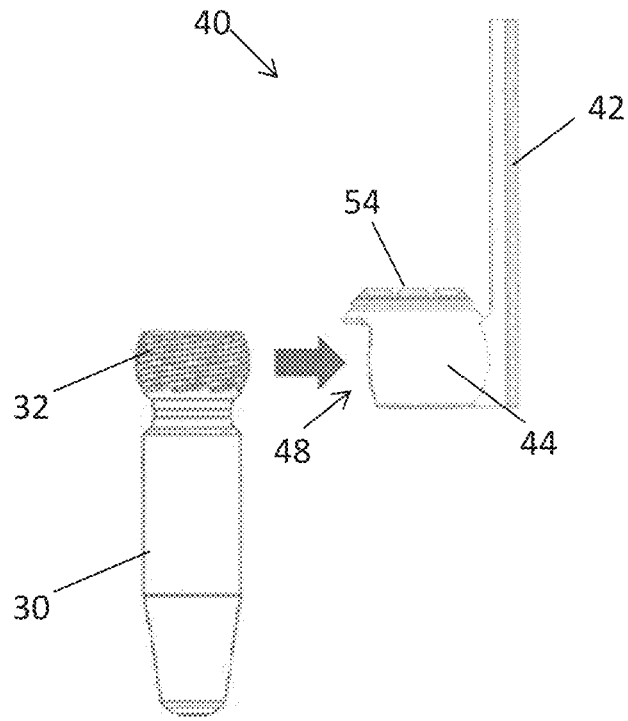
Figure 3H:
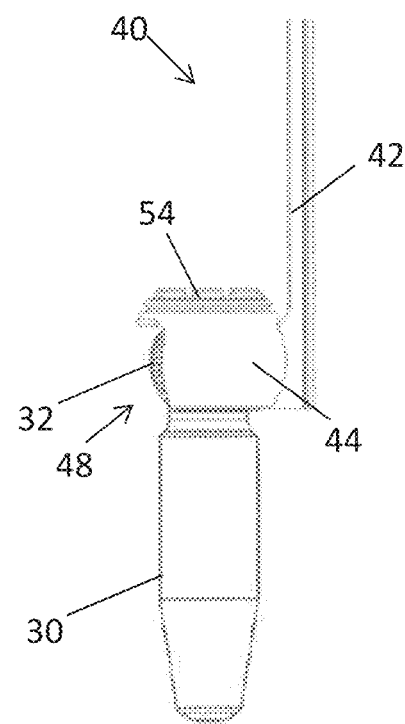
Figure 3I:
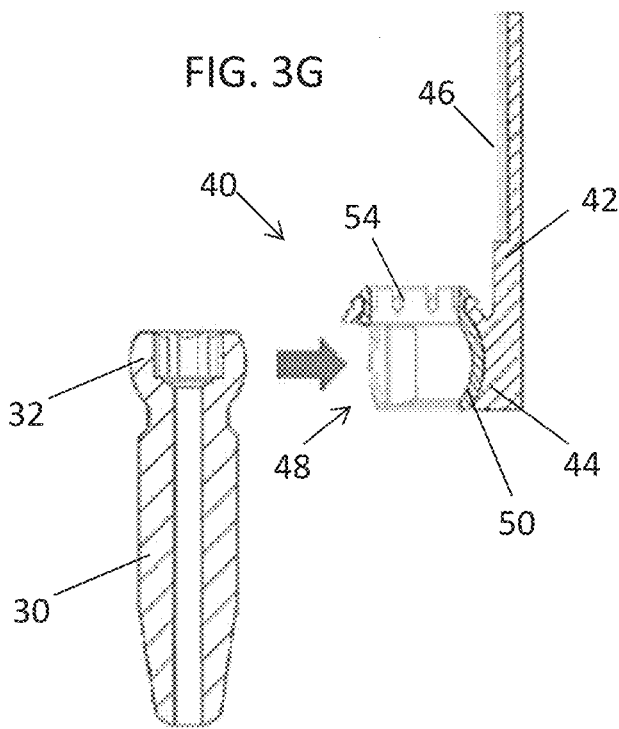
Figure 3J:
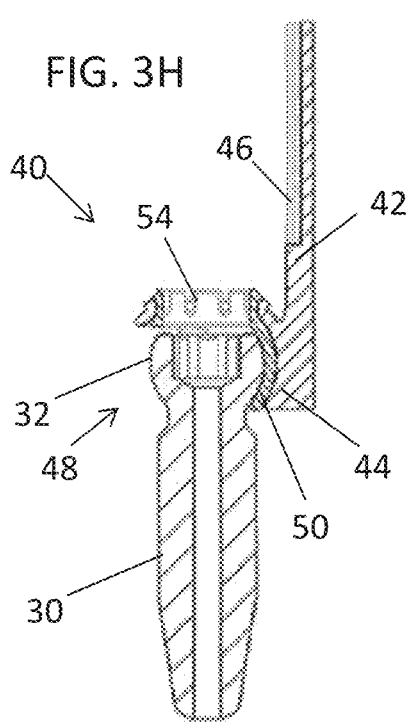
Figures 3K, 3L, 3M:
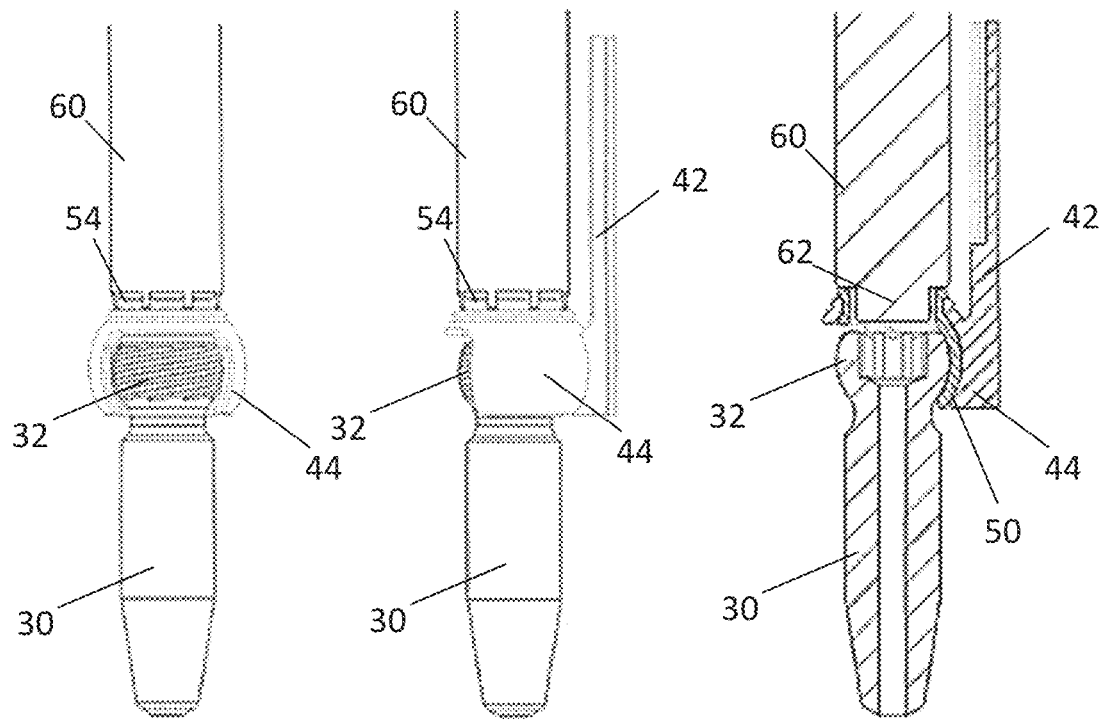
Figures 3N, 3O, 3P:
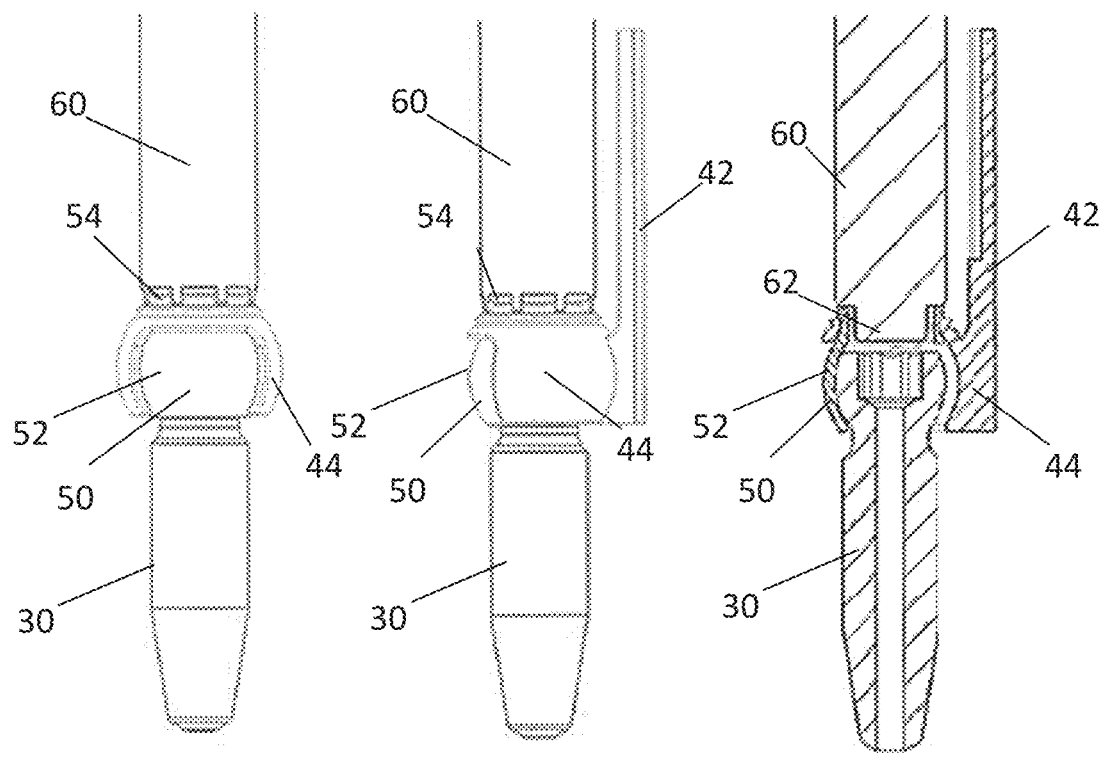

FIGS. 3A-3P provide further details of shim or screw mount 40, which may be used to connect blade 20 to screw 30, for example. The shim or screw mount 40 may include extension portion 42 and connection portion or head portion 44. The extension portion 42 may be in the form of an elongated member extending from a proximal end to a distal end. The extension portion 42 may include track 46 along a front surface. The track 46 may include one or more recesses or grooves extending along a longitudinal length of the extension portion 42. The track 46 is configured to engage and mate with a corresponding track portion 62 on driver 60.

The connection portion or head portion 44 of the screw mount 40 may be in the form of an outer spherical portion. The outer spherical portion of the head portion 44 may be generally rounded or spherical in shape and may be generally hollow within. The head portion 44 is preferably sized and shaped to receive at least a portion of the head 32 of screw member 30 therein. The head portion 44 preferably defines opening or aperture 48 in order to provide for side-loading of the screw member 30. The bottom of the head portion 44 also includes an opening configured to receive a portion of the shaft of the screw 30. The head portion 44 may be connected to the extension portion 42 at a distal end of the extension portion 42.

The head portion 44 preferably retains internal sphere 50 within. The internal sphere 50 may be sized and shaped to be retained within the head portion 44 of the screw mount 40. The internal sphere 50 also includes an opening configured to receive a portion of the shaft of the screw 30. The internal sphere 50 is preferably configured to rotate with respect to the head portion 44 of the screw mount 40. Internal sphere 50 may extend through an opening in the top of the head portion 44 such that the internal sphere is able to engage with driver 60. The internal sphere 50 may have an opening or aperture corresponding to aperture 48 in the head portion 44. FIGS. 3A-3C show an unlocked position of the internal sphere 50 such that the side-opening in the internal sphere 50 is aligned with the side-opening in the head portion 44. When unlocked, the screw member 30 may be side loaded into the screw mount 40.

FIGS. 3D-F depict screw mount 40 in a locked position (with the screw 30 absent). In other words, the internal sphere 50 is rotated, for example, by driver 60, such that the aperture 48 of the head portion 44 is substantially blocked by side wall 52 of the internal sphere 50, thereby locking the screw member 30 within the head portion 44 of the screw mount 40 in the locked position.

In one embodiment, only the inner sphere 50 is able to rotate. In an alternative embodiment, the two spherical members 44, 50 are each able to rotate independently of one another. Once the screw 30 is inserted into the internal sphere 50, the internal sphere 50 is rotated, for example, 180 degrees, to block the screw head 32 from being removed from the direction that it was inserted. The external sphere 44 contains the screw 30 from being removed from the back side. A physical stop may be provided to give the surgeon feedback to know when the internal sphere 50 has been rotated to the locked position. A feature 54 on the top of the internal sphere 50 may be utilized to allow the driver 60 to mate with the sphere 50 and turn it. The feature 54 may include one or more recesses and/or protrusion, for example, having a round, triangular, squared, polygonal, star, torx, irregular, uniform, non-uniform, offset, staggered and/or tapered shape configured to engage with the distal tip 64 of the driver 60. The outer sphere 44 is retained by the retractor blade 20 to keep it from spinning with the inner sphere 50. The screw 30 can retain its ability to rotate and pivot to a desired angle. The internal sphere 50 can be rotated, for example another 180 degrees, to unblock the screw 30 for removal from the screw mount 40.

As shown in FIGS. 3G-3P, the steps for inserting screw 30 are shown for side-loading the screw 30 into the mount 40. In FIGS. 3G and 3I, the head 32 of the screw 30 is aligned with the opening 48 in the outer sphere 44. The inner sphere 50 is in the unlocked position. In FIGS. 3H and 3J, the head 32 of the screw is inserted in the inner sphere 50 that is positioned inside the outer sphere 44. FIGS. 3K-3M show driver 60 engaging the top of inner sphere 50. FIGS. 3N-3P show the inner sphere 50 rotated to the locked position such that the side wall 52 of the inner sphere 50 blocks the aperture 48 of the outer sphere 44.

Figure 4A:
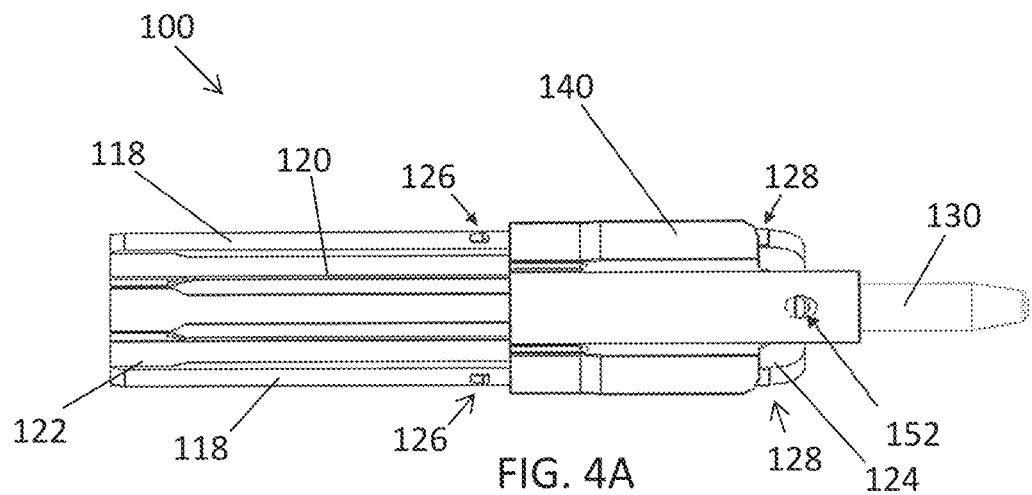
FIGS. 4A-4C show attachment of a retractor blade member to a pedicle screw according to another embodiment.
Figure 4B:
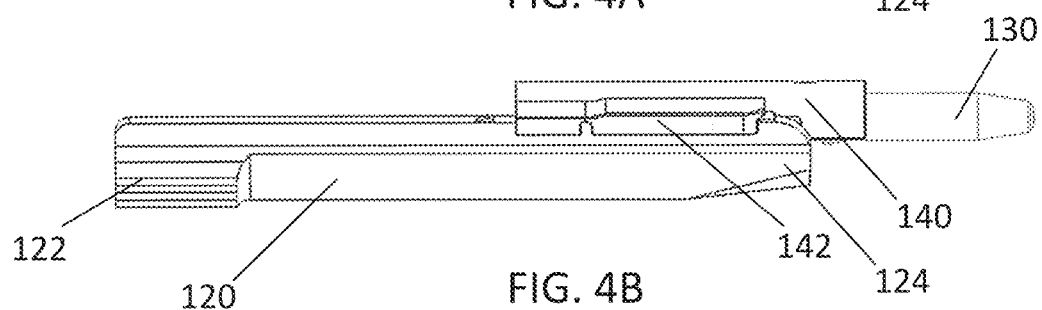
Figure 4C:
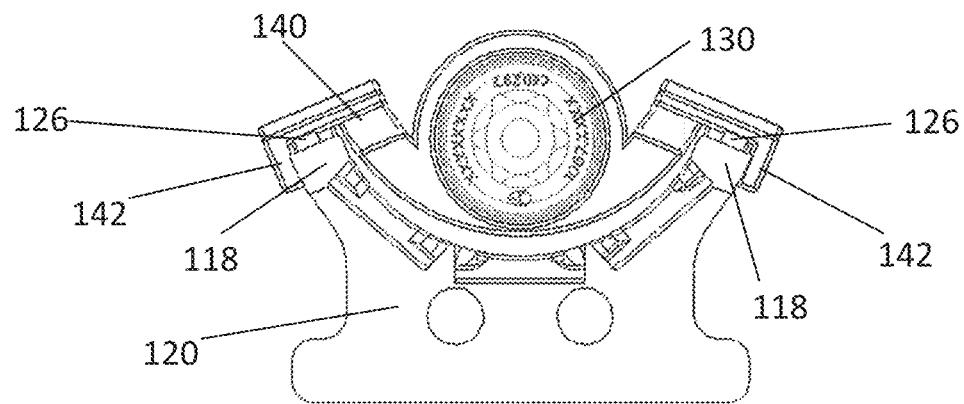

Turning now to FIGS. 4A-4C, another mechanism of attachment between the retractor blade 120 and the pedicle screw 130 is shown. In particular, FIG. 4A depicts a front view of the blade assembly 100 including screw mount or shim 140 connecting the pedicle screw 130 to the retractor blade 120. In this design, the screw mount or shim 140 wraps around the outer edges of the blade 120 to keep it in place. FIG. 4B depicts a side view of an edge 142 of the shim 140 engaged with the blade 120. The blade 120 extends from a proximal end portion 122 to a distal end portion 124 configured to engage with and retract soft tissues and/or muscle. The blade 120 has a generally curved inner portion configure to mate with a generally curved portion of the shim 140. The blade 120 includes two extensions or end portions 118 at the outer most portions of the curved blade. These end portions 118 may extend along a portion or an entire length of the blade 120 from the proximal end 122 to the distal end 124. The shim 114 includes extension portions with edges 142 configured to surround the end portions 118 of the blade 120. FIG. 4C shows a top view of the assembly 100.

When installing the assembly 100 or a portion thereof, the bone screw 130 may be threaded in to the pedicle and the screw mount 140 may be added before or after the bone screw 130 is engaged with the pedicle. With the bone screw 130 and shim 140 in place, the retractor blade 120 slides into the shim 140. One or more locks 126 (e.g., two locks 126 shown in FIG. 4A) may be provided on the outer edges or end portions 118 of the blade 120 such that the locks 126 engage once the screw 130 is fully engaged inside the bone. One or more stops 128 (e.g., two stops 128 shown in FIG. 4A) may also be provided on the blade 120 at the distal end 124 to prevent the shim 140 from backing out proximally during the surgery. A removal slot and/or tab 152 may be operable by a removal tool to disengage the distal end of the shim 140 from the head of the screw 130, thereby allowing the shim 140 to slide back up the outer edges of the blade 120 and separate from the blade 120.

Figure 5A:
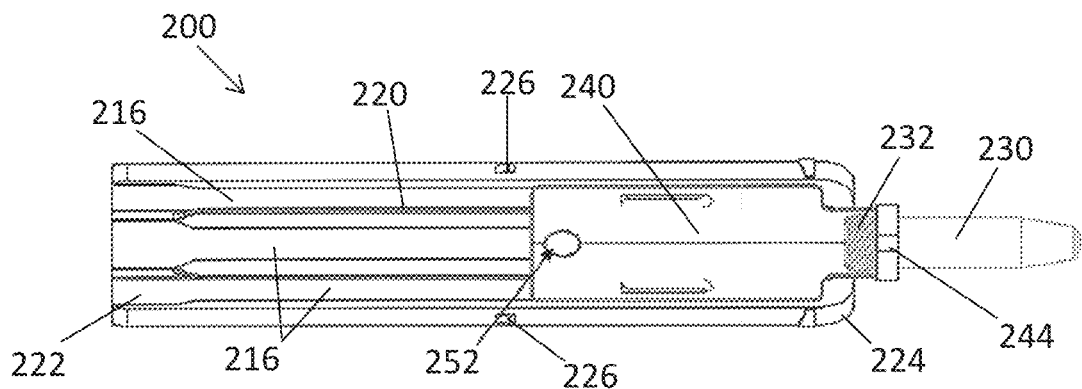
FIGS. 5A-5C show attachment of a retractor blade member to a pedicle screw according to yet another embodiment.
Figure 5B:
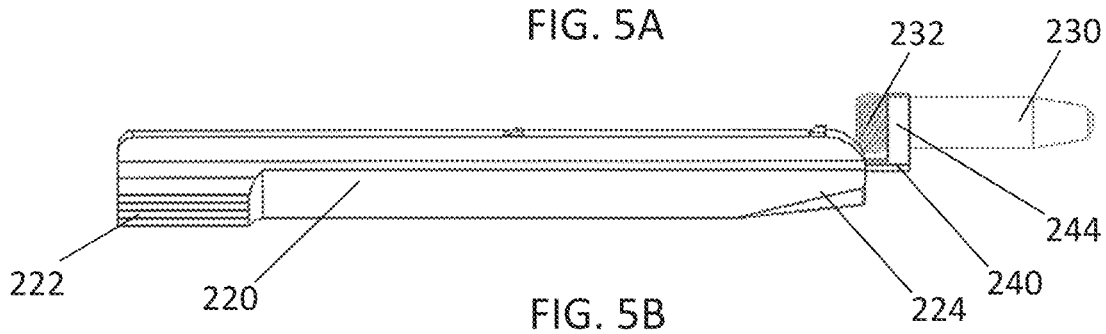
Figure 5C:
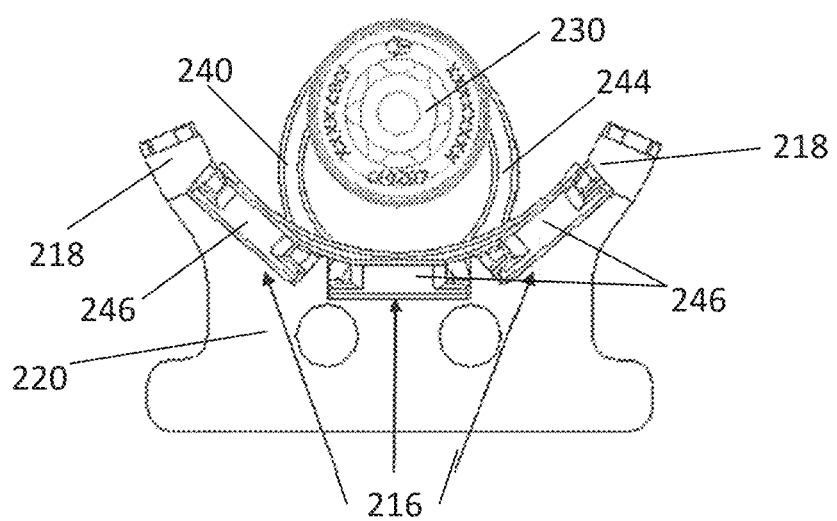

FIGS. 5A-5C depict an alternative version of a blade assembly 200 where the screw mount or shim 240 engages interior rails 216 on the blade 220. In FIG. 5A, a front view of the blade assembly 200 is shown including screw mount or shim 240 connecting the pedicle screw 230 to the retractor blade 220. In this design, the shim 240 slides down the interior rails 216 of the blade 220 to keep the shim 240 in place. FIG. 5B depicts a side view of the shim 240 engaged with the blade 220. The blade 220 extends from a proximal end portion 222 to a distal end portion 224 configured to engage with and retract soft tissues. In one embodiment, the blade 220 is identical to blade 120 such that shim 240 and shim 140 are interchangeable with the same blade 120, 220 design. One or more locks 226 (e.g., two locks 226 shown in FIG. 5A) may be provided on the outer edges or end portions of the blade 220, for example, if shim 140 where selected.

The blade 220 may have a generally curved inner portion having one or more rails 216, for example, in the form of channels or grooves, defined along a portion or an entire length of the blade 220 from the proximal end 222 to the distal end 224. The shim 214 includes corresponding rails 246, for example, in the form of ridges or tongues, configured to be received within and slidably engage the rails 216 of the blade 220. FIG. 5C shows a top view of the assembly 200. The shim 214 also includes a partial or complete ring 244 configured to at least partially surround or rest below the head portion 242 of the screw 230. As the bone screw 230 is driven into the pedicle, one or more dimples may be centered inside the rails 216 (e.g., the outer two rails 216) of the blade 220 that engage with the shim 240 while the screw 230 is being driven into the bone. A removal tool can be used to allow the shim 240 to slide back up the rails 216 and separate from the blade 220.

Turning now to FIGS. 6A-6D, another mechanism of attachment between the retractor blade 220 and the pedicle screw 330 is shown. In particular, FIG. 6A depicts a front view of the blade assembly 300 including screw mount or rotating shim 340 connecting the pedicle screw 330 to the retractor blade 320. In this design, the shim 340 is configured to rotate or spin in order to catch and lock or unlock the pedicle screw 330 to the blade 220.

The blade 220 may have a generally curved inner portion having one or more rails 316, for example, in the form of channels or grooves, defined along a portion or an entire length of the blade 320. Similar to assembly 200, the shim 340 may be configured to slide down the interior rail 316 of the blade 320 to keep the shim 340 in place. In this case, the rail 316 may be a single, central rail 316 in the form of an internal T-slot, for example. The shim 314 includes a corresponding rail 346, for example, in the form of a ridge or tongue, configured to be received within and slidably engage the rail 316 of the blade 320. In particular, the shim 314 may include a single, central T-rail 346. FIG. 6D shows a top view of the assembly 300. The shim 314 also includes a partial ring 344 configured to at least partially surround or rest beneath the head portion 342 of the screw 330. The ring 344 includes an opening to allow for side loading of the screw 330 onto the shim 340.

The pedicle screw 330 may be inserted into the pedicle, for example, using an open or MIS approach. The rotating shim 340 may be inserted into the retractor blade 320 via the internal T-slot 316 and T-rail 346. The rotating shim 340 can be locked in place using one or more dimples, for example. With the shim 340 inserted, the retractor blade 320 and shim 340 can be inserted into the incision and moved (e.g., cephalad and/or caudal) until the shim 340 hooks onto the pedicle screw 330. The shim 340 may or may not lock to the screw 330. Once attached for all pedicles, the blades 320 may be attached to the retractor body. To disconnect the shim 340 from the screw 330, a tool (e.g., a hex tool) may be configured to rotate the shim 340 (e.g., 180°) while still in the blade 320, thereby allowing for the blades to be retracted further (e.g., cephalad and/or caudal) without being attached to the pedicle screws 330 any further.

FIGS. 7A-7C depict assembly 400 including retractor blade 420, shim 440, and pedicle screw 430. In this embodiment, the shim 440 is in the form of a split collet. For example, the shim 440 may include two separate arms separated by a longitudinal slot having a ring 444 at a distal-most end. A slight interference between the collet 440 and screw head 432 allows the shim 440 to be clicked over the shank of the screw 430. The shim 440 may snap over the screw head 432 and be inserted through the incision with the pedicle screw 430. Once the screw 430 is in place, the retractor blade 420 may be inserted and slid over the shim 440 using an internal T-slot similar to that described in assembly 300. There may be no secondary locking between the screw 430 and the shim 440 and retractor blade 420. Alternatively, there may be an extended groove or slot 448 for addition tightening. As best seen in FIG. 7B, as the retractor blades 420 slides down, there is an elongated slot 448 in the shim interference causing the collet 440 to tighten further, thereby better locking screw 430 to the shim 440. With the blades 420 connected to the shims 440 and screws 430, the retractor can be attached to the retractor blades 420. To remove the shim 440, a separate tool can be used to loosen the connection between the shims 440 and the screw 430 to remove the shim 440 from the retractor blade 420.

FIGS. 8A-8C illustrate an alternative embodiment for attachment between the pedicle screw 530 and the blade 520. In this embodiment, the screw 530 is directly attached to the blade 520 using a wire, filament, fiber, or cable 540. The cable 540 may include any suitable elongate element configured to engage the pedicle screw and the blade 520 at one or more points of contact. For example, the retractor blade 520 may have the cable 540 attached on one end, for example, at the top of the blade 520. The cable 540 may be routed down the blade tip where it will form a hoop and be routed back up to the top of the blade 520. The cable 540 may extend through one or more openings in the blade 520, for example. The shank of the screw 530 may be threaded into the pedicle using a driver, for example. Prior to removing the driver, a slackened hoop of cable 540 may be placed around the driver and the blade 520 may be inserted down the incision using the driver as a guide. Once the retractor blade 520 reaches its predetermined depth, the cable 540 can be tightened, for example, using one or more thumb knobs 550, thereby taking up the slack and tightening the cable 540 around the screw 530. Thumb knobs 550 may be in the form of wheels or cylinders, for example, attached to the proximal end of the blade 520. The thumb knobs 550 may be configured to rotate such that the cable 540 winds around the base of the knobs 550. The driver can then be detached and removed from the incision. If needed, distraction of the disc space can take place, for example, using the pedicle screws 530. To remove the retractor blade 520 from the screw 530 after the retraction is no longer needed, the cable 540 can be slacked again or disconnected entirely from one or both ends. As the blades 520 are removed, the cable 540 can unwind and pull free from the screw 530.

Referring to FIGS. 9A-9F, a screw mount 640 in accordance with another embodiment which is configured to connect the pedicle screw member 30 to a blade 620 will be described. The mount 640 includes an extension portion 642 and a head portion 660. In the illustrated embodiment, the extension portion 642 defines tracks 644, 645 and 646, for example, in the form of recesses extending along a longitudinal length of the extension portion 642. The track 644 is configured to receive a slidable locking mechanism 670 (see FIG. 9F), as will be described in more detail hereinafter. The tracks 645 and 646 are configured to slidably engage and mate with rails on a corresponding blade 620, as will be described with reference to FIGS. 10E to 10J. The outside surfaces of the extension portion 642 opposite of the tracks 646 define an external track configured to mate with a corresponding track portion 686 on a driver 680, as will be described with reference to FIGS. 10A-10D. The extension portion 642 of the illustrated mount 640 also defines a pair of driver mating openings 641 and a pair of blade mating openings 647. Each of the driver mating openings 641 is open to receive a biased tab 687 on the drive 680 as illustrated in FIGS. 10A-10C. A biased retaining member 648 is positioned in each blade mating opening 647 and includes a lip 649 configured to engage a slot 626 in the blade 620 as illustrated in FIGS. 10I-10J.

The head portion 660 of the screw mount 640 is sized and configured to receive the head 32 from the screw member 30. In particular, the head portion 660 in the current embodiment defines an internal, concave wall 662 about a chamber 664 with end openings 663 and 665. The screw head 32 may be positioned in the chamber 664 by passing through either end opening 663, 665. In the illustrated embodiment, the head 660 is configured with a stop 667, such that the screw head 32 is received through opening 663 and contacts the stop 667 to properly align the screw head 32 within the concave surfaces 656, 662. The chamber 664 generally has a diameter larger than the diameter of the screw head 32. A retaining member 650 having a body 652 extends from the extension portion 642 such that a free end 654 thereof extends into the chamber 664. The free end 654 defines a concave surface 656 which engages a portion of the screw head 32 such that the screw head 32 is retained between the inner wall surface 662 and the free end surface 656. The surfaces 656, 662 hold above and below the centerline of the screw head 32 so that the screw 30 cannot be removed in an up or down movement. Slits 653 in the extension portion 642 allow the free end 654 of the retaining member 650 to move radially outward as the screw head 32 enters or exits the chamber 664. The retaining member 650 is biased to an inward, engaging position. Even in the engaged position, the chamber 664 is slightly oversized relative to the screw head 32 to ensure a loose fit and easy screw manipulation without damaging the screw head features. The screw 30 will be able to rotate and pivot without resistance.

Figure 9A:
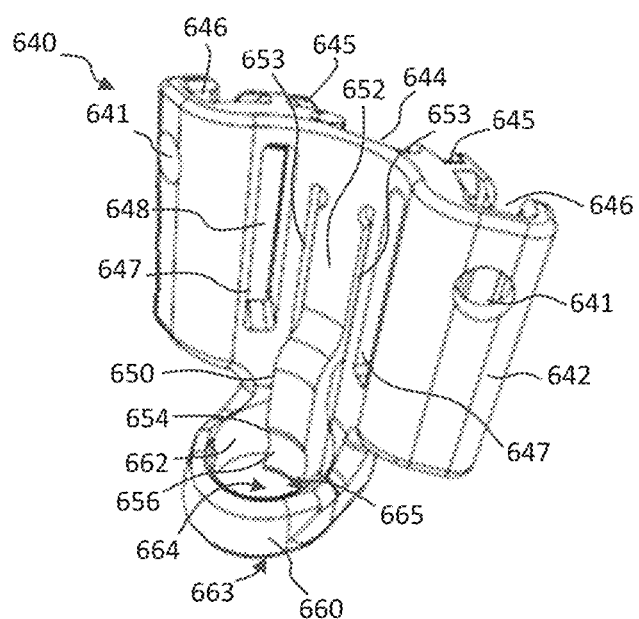
FIGS. 9A-9F illustrate an alternative screw mount suitable for use in attaching a pedicle screw to the retractor blade.
Figure 9B:
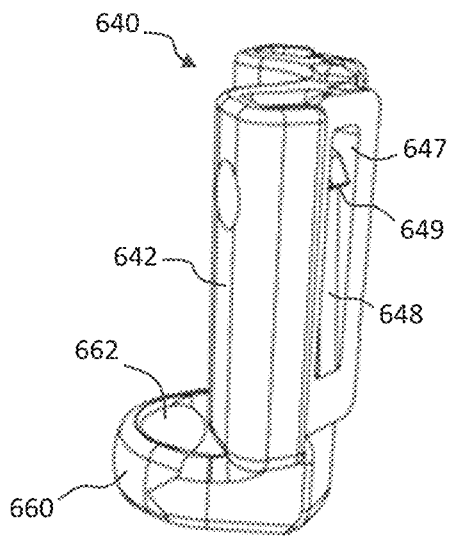
Figure 9C:
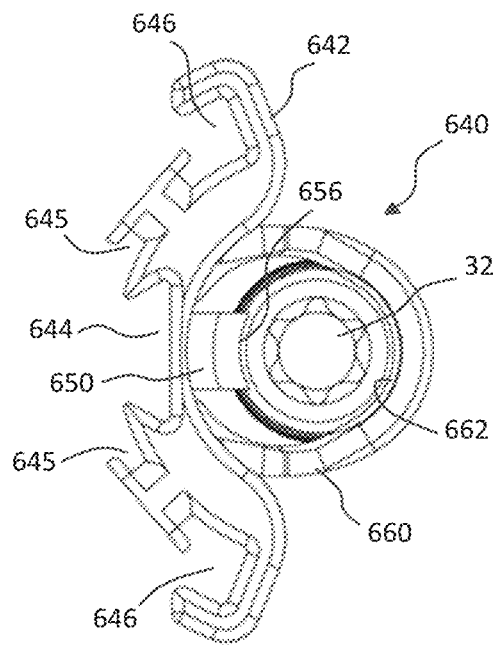
Figure 9D:
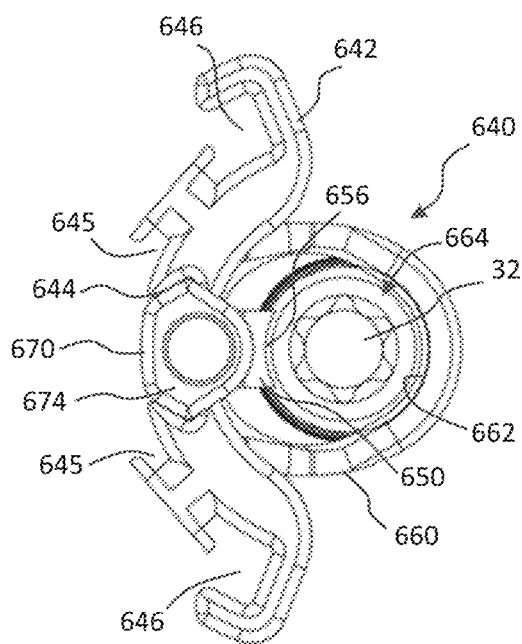
Figure 9E:
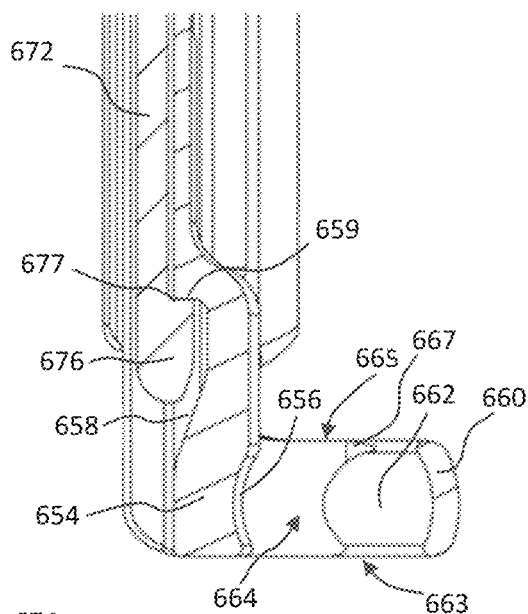
Figure 9F:
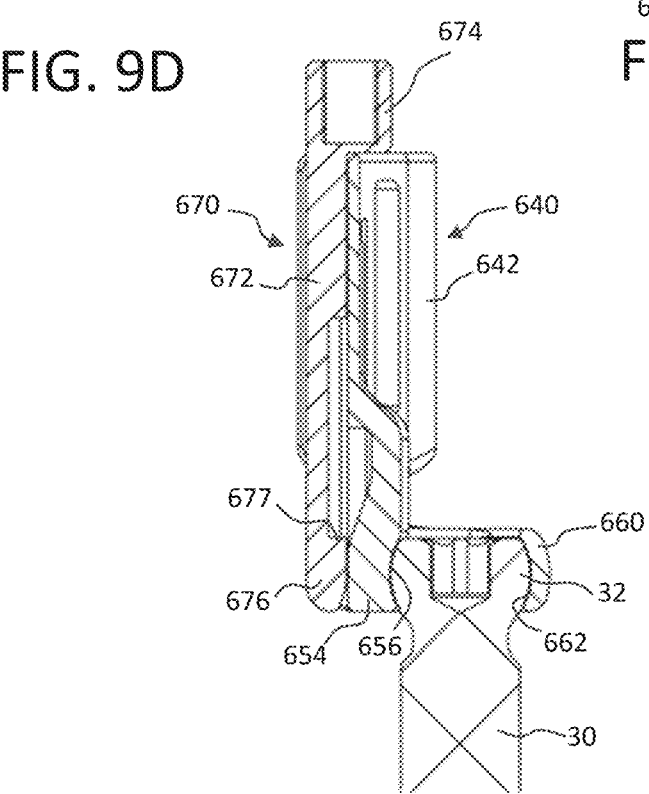

Referring to FIGS. 9D-9F, the locking mechanism 670 is slidable along the track 644 from an unlocked position (FIG. 9E) to a locked position (FIG. 9F). The locking mechanism 670 includes an elongate body 672 with a head 674 at the proximal end and an engagement portion 676 at the distal end. In the locked position, the head 674 is depressed such that the engagement portion 676 moves into engagement with the free end 654 of the retaining mechanism 650, thereby locking the free end surface 656 in engagement with the screw head 32. As will be described hereinafter, the head 674 may be depressed manually and retained by the blade 620. For entry or removal of the screw head 32 from the chamber 664, the locking mechanism 670 is moved to the unlocked position illustrated in FIG. 9E. In the unlocked position, the engagement portion 676 is aligned with a notch 658 in the body 652 of the retaining member 650, such that the free end 654 may move radially outwardly to allow the screw head 32 to pass. Contact surfaces 659, 677 in the notch 658 and on the engagement portion 676 define a stop for the locking mechanism 670.

Figure 10A:
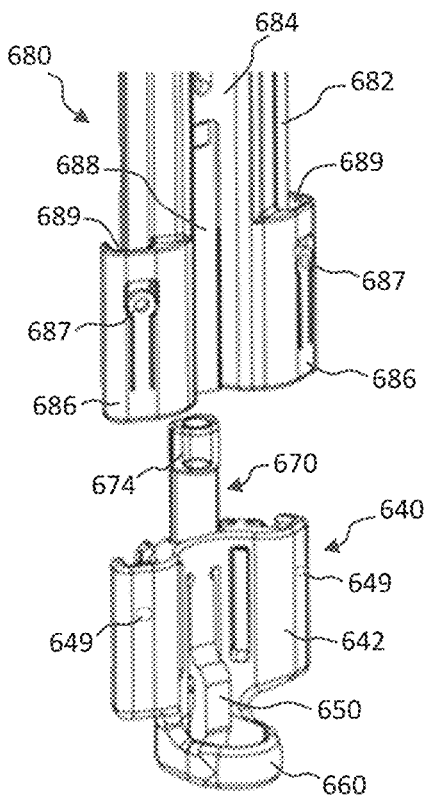
Figure 10B:
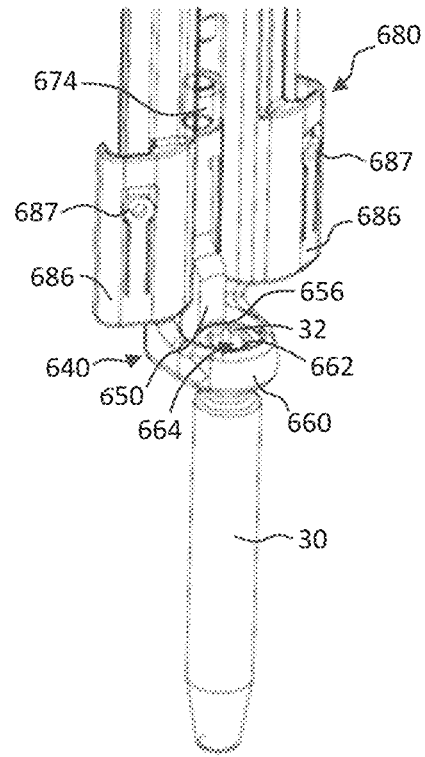
Figure 10C:
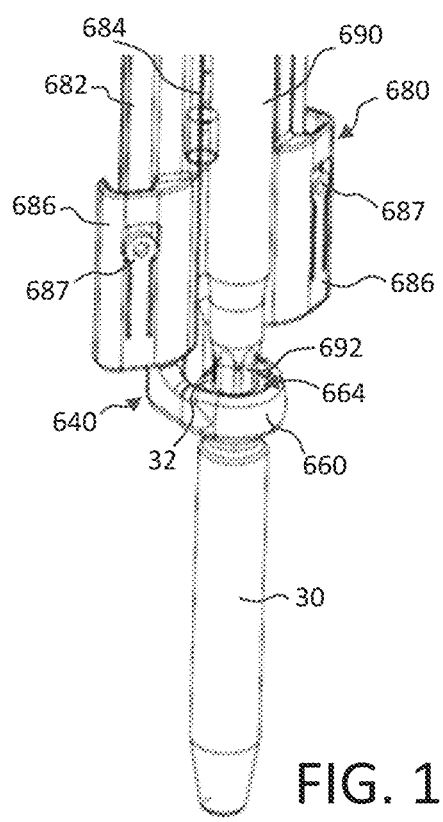

Turning to FIGS. 10A-10K, a system and method for attaching a pedicle screw member 30 to a blade 620 utilizing the screw mount 640 will be described. Referring to FIG. 10A, the driver 680 includes a body 682 extending between a proximal end and a distal end with the distal end defining distal portions 686 configured to engage the screw mount 640. Each distal portion 686 defines an internal track 689 configured to receive and engage a portion of the extension portion 642. Each distal portion 686 also includes a biased tab 687 configured to engage a respective driver mating opening 641 on the extended portion 642 of the screw mount. The biased tabs 687 releasably retain the driver 680 on the screw mount 640.

Figure 10D:
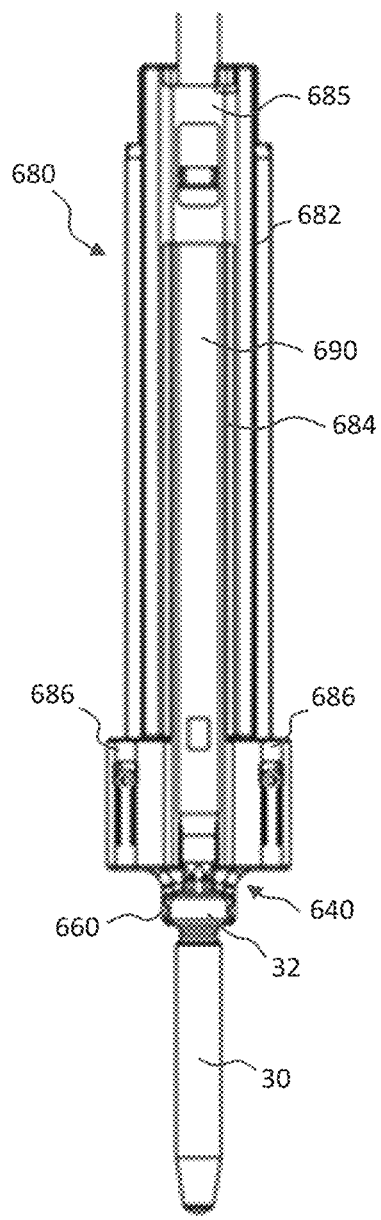
Figure 10E:
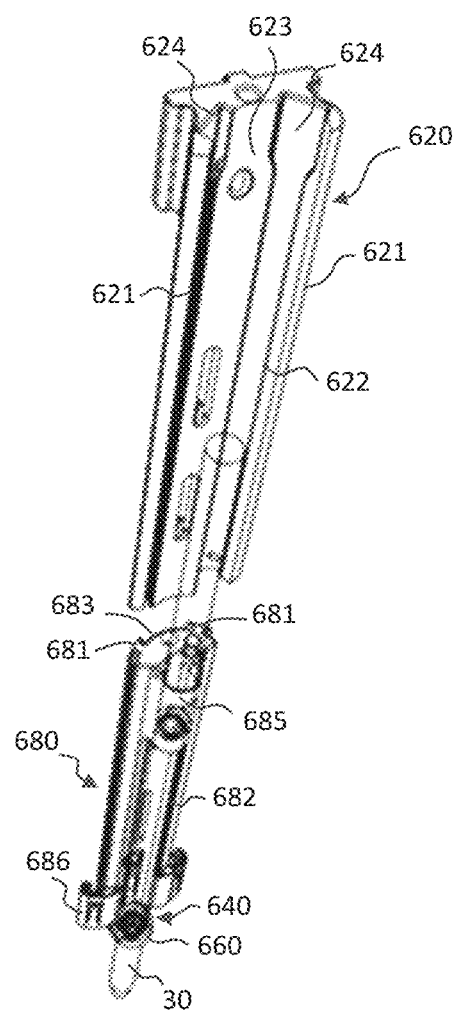

Referring to FIGS. 10A, 10D and 10E, the driver body 682 defines a driver tool slot 684 extending from the proximal end to the distal end. In the illustrated embodiment, a cylindrical guide 685 extends from the proximal end of the body 682 about the slot 684 to assist in maintaining the driver tool 690 aligned within the slot 684. The driver tool 690 includes a distal tip 692 configured to engage the screw 30. The distal tip 692 may be of any suitable shape and configuration including, but not limited to, round, triangular, squared, polygonal, star, torx, irregular, uniform, non-uniform, offset, staggered and/or tapered. The body 682 of the driver 680 also defines one or more tracks 681, 683 on the rear surface thereof. The tracks 681, 683 are configured to guide the respective blade 620. As shown in FIG. 10E, the illustrative blade 620 includes a body 622 extending from a proximal end to a distal end, with outer rails 621 and a central rail 623 defining slots 624. The outer rails 621 align with the tracks 681 and the central rail 623 aligns with the track 683.

A series of steps, which may be used to install the pedicle screw 30 in bone and mount a retractor blade 620 thereto is further described. Any of these steps may be performed before or during the operation in any suitable order. The screw mounts 640 may be available as a kit or set, for example, in a caddy sitting upright (not shown). With reference on FIGS. 10A-10C, as an initial step, a desired number of screw mounts 640 will be attached to respective drivers 680. The secondary slot 688 in the distal end of the driver body 682 receives the head portion 674 of the locking mechanism 670 such that the locking mechanism 670 remains in the unlocked position. With the locking mechanism 670 in the unlocked position, a screw 30 of a desired length will be inserted through the bottom opening 663 of the head portion 660. With the screw head 32 within the chamber 664, the head 674 of the locking mechanism 670 is depressed to move the locking mechanism 670 to the locked position such that the screw 30 is locked in place as shown in FIG. 10B. The driver tool 690 is positioned within the driver slot 684 and the distal tip 692 of the driver tool 690 engages the screw head 32 as illustrated in FIGS. 10C and 10D.

At the surgical site, a Jamshidi needle and k-wire may be placed into the pedicle. A series of cannulas may be inserted over the k-wire to dilate the tissue and obtain the blade length. The cannulas may then be removed, leaving the k-wire in place. The driver assembly, including the screw member 30 and screw mount 640 connected to the driver 680, may pass over the k-wire and the screw member 30 may be inserted into the pedicle (e.g., threaded into the pedicle). To reduce tissue disruption, the driver 680 along with the screw mount 640 will be free to spin independent of the driver tool 690. With the screw 30 at the necessary depth, the required blade length may be measured off of the driver 6680.

Figure 10F:
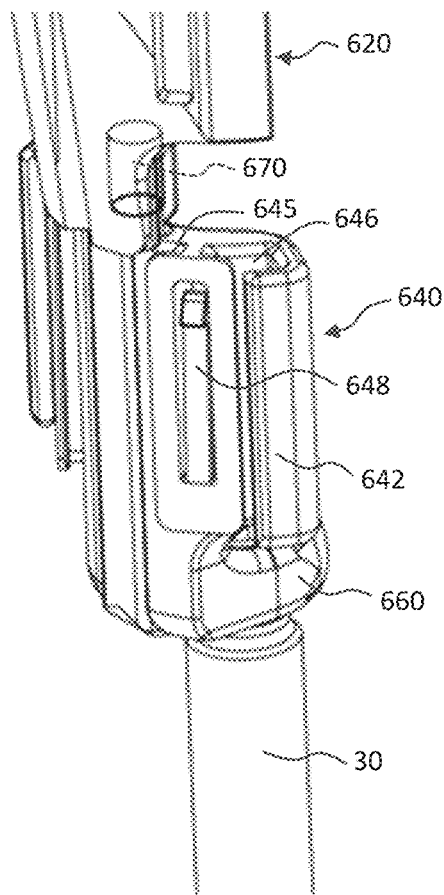
Figure 10G:
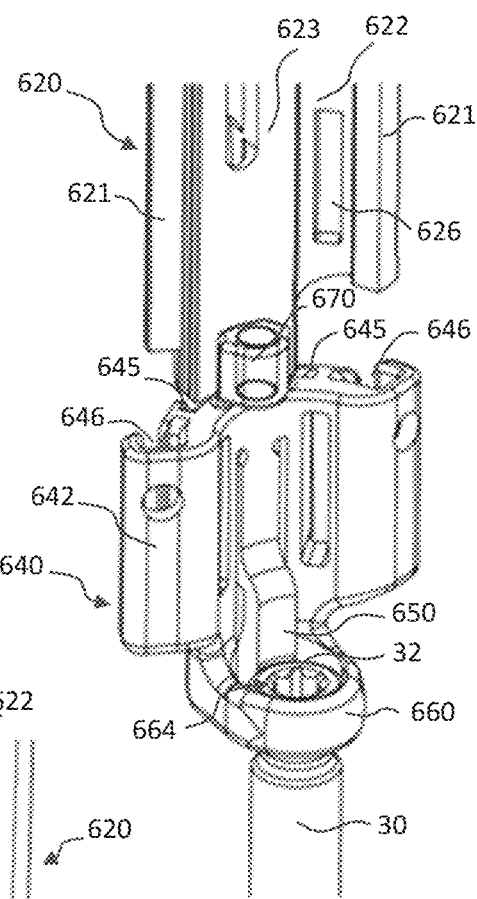
Figure 10H:
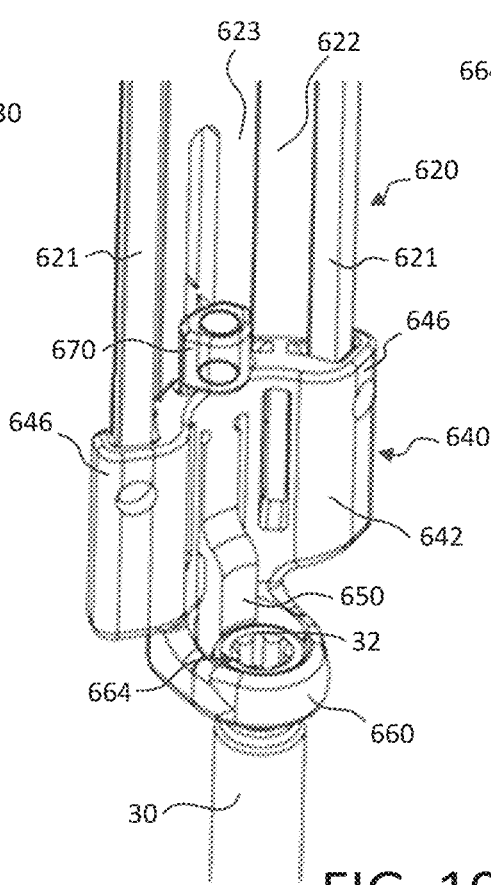

Turning now to FIG. 10E, prior to disconnecting the driver 680 from the screw mount 640, the blade 620 may be engaged with the driver 680. With a blade handle (not shown) attached to the blade 620, the blade 620 will be inserted from the top down with the outer rails 621 engaging with the tracks 681 and the central rail 623 engaging with the track 683. FIGS. 10F-10J illustrate the interconnection of the blade 620 with the screw mount 640. In these figures, the driver 680 is omitted for clarity, however, the driver 680 will be maintained in position until the blade 620 is fully inserted. Referring to FIGS. 10F-10H, as the blade 620 is inserted, the outer rails 621 are received in the tracks 646 and the central rail 623 is received in the track 645. As shown in FIGS. 10I-10J, as the blade 620 moves into the screw mount 640, the lip 649 of each biased retaining member 648 is received in a respective slot 626 in the blade 620. The distal end 627 of the slot 626 defines a stop for the lip 649. The engagement of the lip 629 within the slot 626 defines a range of motion over which the blade 620 is axially moveable relative to the screw mount 640. In at least one embodiment, the blade 620 and screw mount 640 will have at least 10 mm of passive translation between them.

With the blade 620 connected to the screw mount 640, the driver 680 will then be disconnected and removed from the screw mount 640 and blade 620 by pulling up on it, as illustrated in FIG. 10K. The blade handle on the blade 620 will be used to maneuver the initial blade to allow for easy insertion of additional screws, screw mounts, and drivers, as desired. The respective blades will be introduced in the same fashion as the first.

In one exemplary procedure utilizing the blades 620 and screw mounts 640, after the screws, screw mounts, and blades are inserted in the pedicles, the retractor will be introduced in a manner to that described above. The cranial and caudal retractor arms will be able to freely slide to easily align with the blades. The retractor will be attached from a side approach in the lateral position. The blades will automatically lock onto the retractor posts at any angle through the use of two mating stargrinds. A spring loaded button on the blades will slide into a groove on the retractor post to rigidly lock them together. The retractor arms will then be reengaged and able to be independently retracted with the use of a hex driver. The use of a worm drive will allow the blade to pivot an infinite amount in either direction.

With the blades positioned as desired, a medial arm and blade will be attached to the retractor. The arm will attach to the retractor from a top down approach and the medial blade will attach to the medial arm from an in line approach. The arm will include a linear retraction mechanism and a passive translation mechanism to allow the blade to be positioned midway between the cranial and caudal blades. The arm will also contain a mechanism to angle the blade in a medial/lateral direction. A blade handle will attach to the blade for easier control during manual retraction prior to attaching to the arm. The medial blade will utilize a passive translation member to allow the blade to be lengthened or shortened as desired. Likewise, a lateral arm and blade may be attached and utilized.

At the end of the case, the surgeon will disconnect the screw mounts from the screws, attach modular MIS tulips, for example, remove the medial and lateral blades and remove the cranial and caudal blades and the retractor. The remainder of the case, insertion of the rod and locking caps, may be performed, for example, using traditional MIS techniques.

The system and method, described with respect to FIGS. 10A-10K, provide a combined capability of retracting and distracting via secure attachment from the blade to the screw. Top down loading of the screw allows for in-situ attachment if necessary. Additionally, the driver acts as dilator for the blade to slide over with less tissue disruption. As an additional benefit, the system provides the ability to lock and unlock from the screw without having to disconnect the blade mount from the blade. Additionally, distraction forces will be on the front half of the sphere which is a part of the strong vertical segment. Passive screw mount translation allows the blades lengths to match any patient anatomy and allows the retractor to sit perfectly on each patient's skin level. Additionally, the passive translation along with the rigid connection of the screw mount to the screws allows the surgeons to pivot the retractor in the cranial/caudal direction as needed without having any tissue creep.

Turning to FIGS. 11A-11E, a system and method for attaching a pedicle screw member 30 to a blade 720 utilizing a tulip screw mount 740 will be described. The tulip screw mount 740 has a slotted configuration having legs defined by a distal body portion 742 that project upwardly from a closed end 744 of the tulip screw mount 740. Leg extensions 745 extend from the body portion 742 above a breakaway feature 747 that is cut into and partially through an external surface of the tulip screw mount 740. The breakaway features 747 can be cut into the tulip body 742 in any number of known manners. An open slot 748 extends from the proximal end 750 of the tulip screw mount 740 to the closed end 744. The closed end 740 defines a seat 746 for a screw head 32.

Figure 11A:
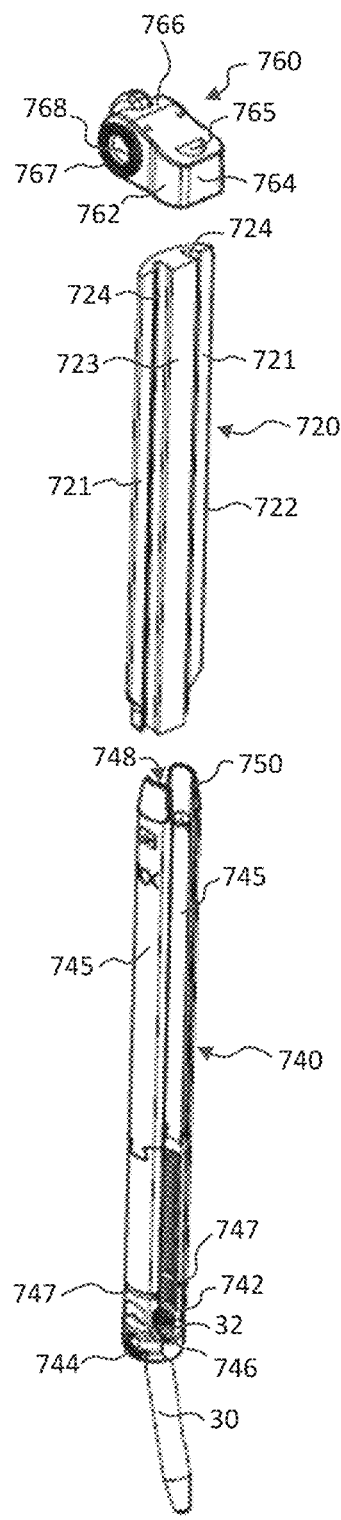
FIGS. 11A-11E illustrate components and a series of steps, which may be used to install a pedicle screw in bone and mount a retractor blade thereto in accordance with another embodiment.
Figure 11B:
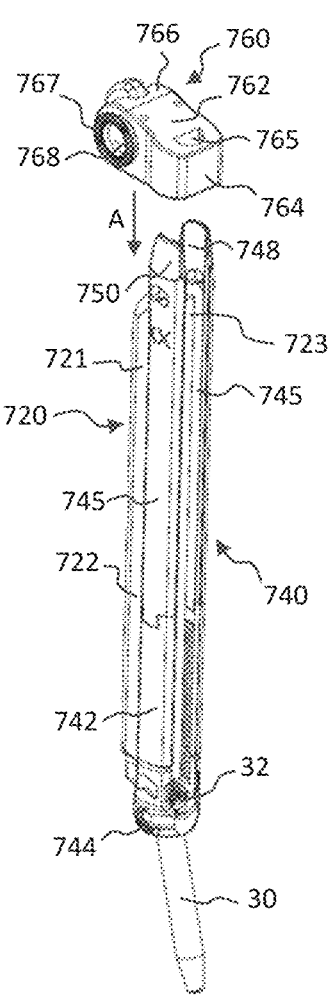
Figure 11C:
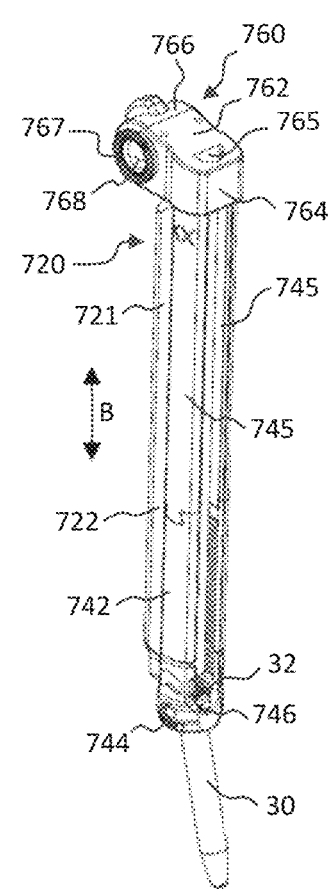

The blade 720 includes a linear blade body 722 with a pair of side rails 721 and a central rail 723 extending the length thereof. A slot 724 extends between the central rail 723 and each respective side rail 721. The central rail 723 is configured to be received in the slot 748 defined by the tulip screw mount 740 as shown in FIG. 11B. In the illustrated embodiment, the central rail 723 is tapered from the free end thereof to the body 722 such that the blade 720 is maintained connected to the tulip screw mount 740.

Once the blade 720 is positioned within the slot 748, a cap 760 is secured on the proximal end 750 of the tulip screw mount 740. The cap 760 has a body 762 extending from a connection end 764 to a pivot end 766. The connection end 764 includes openings thereinto (not shown) which receive and secure the proximal ends of the leg extensions 745 as the cap is moved onto the tulip screw mount 740, as indicated by arrow A in FIG. 11B. With the cap 760 secured on the leg extensions 745, the blade 720 is secured relative to the tulip screw mount 740, however, in the illustrated embodiment, the blade 730 and mount 740 are configured such that the blade 720 is able to translate up and down, as indicated by arrow B in FIG. 11C, relative to the tulip screw mount 740.

The pivot end 766 of the cap 760 includes a transverse through hole 768 configured to receive a post 14 of a retractor system as will be described hereinafter. A plurality of teeth 767 extend about the through hole 768 on each side of the cap body 762.

In an exemplary procedure utilizing the screws 30, tulip screw mounts 740 and blades 720, the surgeons will begin by creating an oblique posterior incision from pedicle to pedicle on one side of the patient and place the MIS screws 30 with the tulip screw mounts 740 into the pedicles. Having the tulip screw mounts 740 already assembled to the pedicle screws 30 allows the connection to be verified prior to insertion into the incision, which will prevent the screw 30 from being placed too deep, and eliminates the need to later attach the tulips in-situ.

With the driver still attached to the screws 30 and acting as a guide, blades 720 are slid down the tulip screw mounts 740, with the central rail 723 extending into the slot 748, to help retract tissue. The blades 720 will be moveable within the tulip screw mounts 740 with the ability to translate up and down with respect thereto. The upward movement is unrestricted and allows the blade 720 to be removed from the tulip screw mounts 740 while a downward movement is restricted by the closed end 744 and bony anatomy. This translation allows the surgeon to place the blade 720 at the ideal height to reduce the most amount of tissue creep.

Figure 11D:
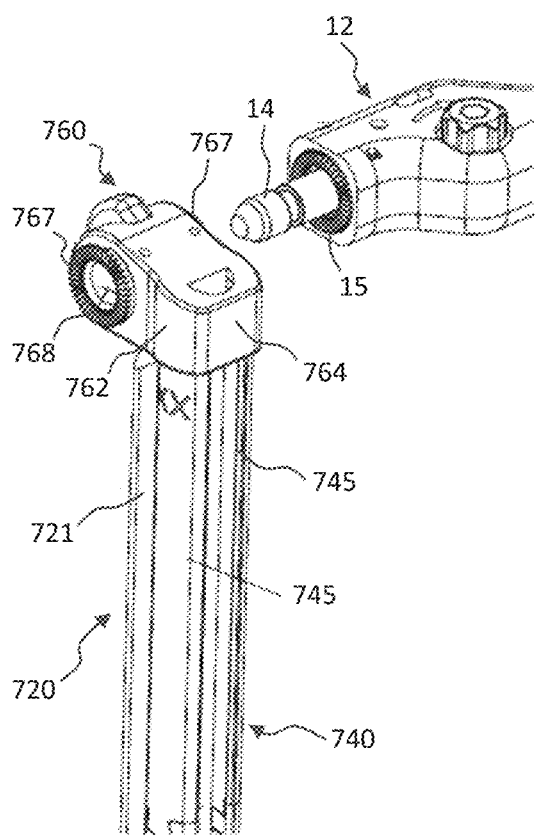
Figure 11E:
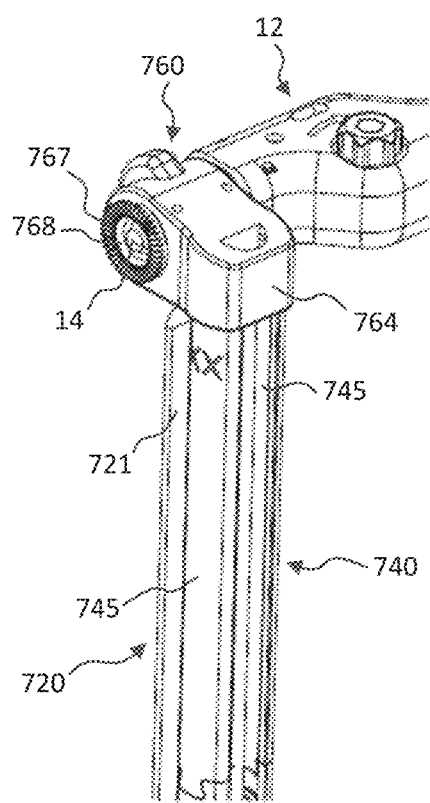

With the blades 720 in place and the driver removed, a cap 760 is fixed to the top of each tulip screw mounts 740 and is axially and rotationally fixed thereto as described above. Referring to FIGS. 11D-11E, the through hole 768 on each cap 769 receives the post 14 of a respective retractor arm 12. Teeth 15 about the post 14 are configured to engage the teeth 767 such that the cap 760, and thereby the blade 720, may be attached to the retractor arm 12 at any desired angle. Once connected to the arms 12, the tulip screw mounts 740, and subsequently the blades 720, will be able to angulate relative to the arms through the use of an angulation mechanism on the retractor arms as well as retract through the use of the retraction mechanism on the retractor frame.

After the interbody cage has been placed, the blades 720 will be slid up slightly but not out of the tulip screw mounts 740. This new position will allow a rod to be introduced into the tulip body 742 and under the blade 720 while the blade 720 continues to retract soft tissue along the remaining portion of the tulip screw mounts 740. To complete the construct, set screws may be introduced prior to detaching the retractor. Before removing the blade 720 from the incision, a rocking motion may be applied to each blade 720 to break off the extended legs 745 at the breaking features 747.

Turning to FIGS. 12A-12D, a system and method for attaching a pedicle screw member 30 to a blade 820 utilizing a tulip screw mount 840 will be described. The tulip screw mount 840 has a slotted configuration having legs defined by a distal body portion 842 that project upwardly from a closed end 844 of the tulip screw mount 840. Leg extensions 845 extend from the body portion 842 above a breakaway feature 847 that is cut into and partially through an external surface of the tulip screw mount 840. The breakaway features 847 can be cut into the tulip body 842 in any number of known manners. An open slot 848 extends from the proximal end 850 of the tulip screw mount 840 to the closed end 844. The closed end 840 defines a seat 846 for a screw head 32.

The blade 820 includes a linear blade body 822 with a pair of side rails 821 and a central rail 823 extending the length thereof. A slot 824 extends between the central rail 823 and each respective side rail 821. The central rail 823 is configured to be received in the slot 848 defined by the tulip screw mount 840 when the blade 820 is inserted into the slot 848, as indicated by arrow C in FIG. 12A. In the illustrated embodiment, the central rail 823 is tapered from the free end thereof to the body 822 such that the blade 820 is maintained connected to the tulip screw mount 840. As such, the blade 820 can be translated axially relative to the tulip screw mount 840, as indicated by arrow D in FIG. 12B, but otherwise is fixed thereto.

The proximal end of the blade 820 includes a pivot connection 860. The pivot connection 860 has a body 862 extending from a connection end 864 to a pivot end 866. The connection end 864 is fixed to the proximal end of the blade body 822. The pivot end 866 of the pivot connection 860 includes a transverse through hole 868 configured to receive a post 14 of a retractor system as will be described hereinafter. A plurality of teeth 867 extend about the through hole 868 on each side of the cap body 862.

In an exemplary procedure utilizing the screws 30, tulip screw mounts 840 and blades 820, the surgeons will begin by creating an oblique posterior incision from pedicle to pedicle on one side of the patient and place the MIS screws 30 with the tulip screw mounts 840 into the pedicles. Having the tulip screw mounts 840 already assembled to the pedicle screws 30 allows the connection to be verified prior to insertion into the incision, which will prevent the screw 30 from being placed too deep, and eliminates the need to later attach the tulips in-situ.

With the driver still attached to the screws 30 and acting as a guide, blades 820 are slid down the tulip screw mounts 840, with the central rail 823 extending into the slot 848, to help retract tissue. The blades 820 will be moveable within the tulip screw mounts 840 with the ability to translate up and down with respect thereto. The upward movement is unrestricted and allows the blade 820 to be removed from the tulip screw mounts 840 while a downward movement is restricted by the closed end 844 and bony anatomy. This translation allows the surgeon to place the blade 820 at the ideal height to reduce the most amount of tissue creep.

Figure 12C:
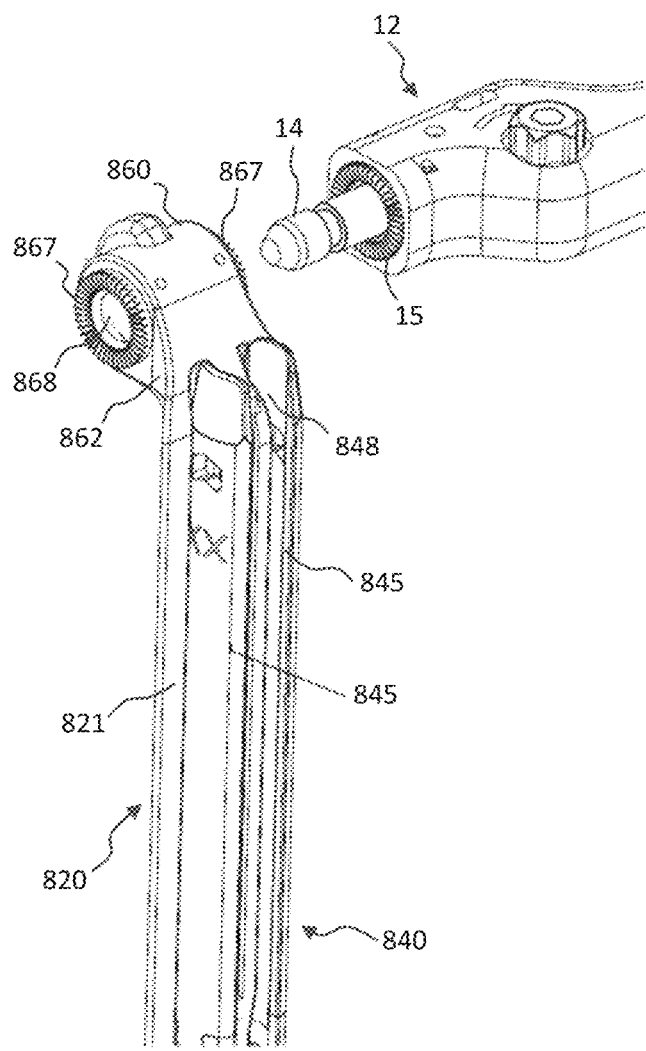
Figure 12D:
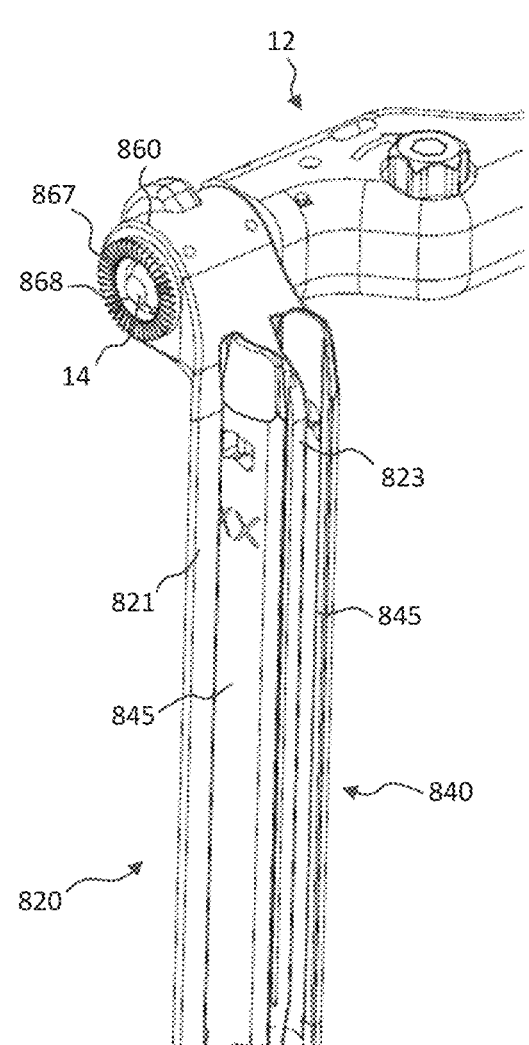

Referring to FIGS. 12C-12D, the through hole 868 on each pivot connection 860 receives the post 14 of a respective retractor arm 12. Teeth 15 about the post 14 are configured to engage the teeth 867 such that the pivot connection 860, and thereby the blade 820, may be attached to the retractor arm 12 at any desired angle. Once connected to the arms 12, the tulip screw mounts 840, and subsequently the blades 820, will be able to angulate relative to the arms through the use of an angulation mechanism on the retractor arms as well as retract through the use of the retraction mechanism on the retractor frame.

After the interbody cage has been placed, the blades 820 will be slid up slightly but not out of the tulip screw mounts 840. This new position will allow a rod to be introduced into the tulip body 842 and under the blade 820 while the blade 820 continues to retract soft tissue along the remaining portion of the tulip screw mounts 840. To complete the construct, set screws may be introduced prior to detaching the retractor. Before removing the blade 820 from the incision, a rocking motion may be applied to each blade 820 to break off the extended legs 845 at the breaking features 847.

Turning to FIGS. 13A-13E, a system and method for attaching a pedicle screw member 30 to a blade 920 utilizing a tulip screw mount 940 will be described. The tulip screw mount 940 has a slotted configuration having legs defined by a distal body portion 942 that project upwardly from a closed end 944 of the tulip screw mount 940. Leg extensions 945 extend from the body portion 942 above a breakaway feature 947 that is cut into and partially through an external surface of the tulip screw mount 940. The breakaway features 947 can be cut into the tulip body 942 in any number of known manners. An open slot 948 extends from the proximal end 950 of the tulip screw mount 940 to the closed end 944. The closed end 940 defines a seat 946 for a screw head 32. A shim 970 having a cylindrical body 972 and a projection 974 are configured to be positioned within the closed end 944 of the tulip screw mount 940 as indicated by arrow E in FIG. 13A. The shim 970 is positioned such that the cylindrical body 972 is within the slot 948 and the projection 974 extends radially therefrom.

Figure 13A:
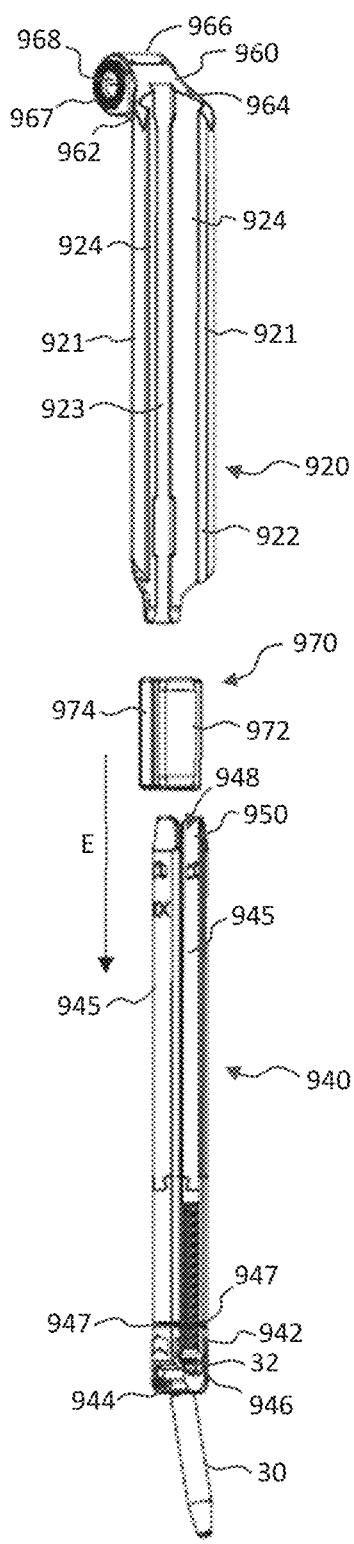
FIGS. 13A-13E illustrate components and a series of steps, which may be used to install a pedicle screw in bone and mount a retractor blade thereto in accordance with another embodiment.
Figure 13B:
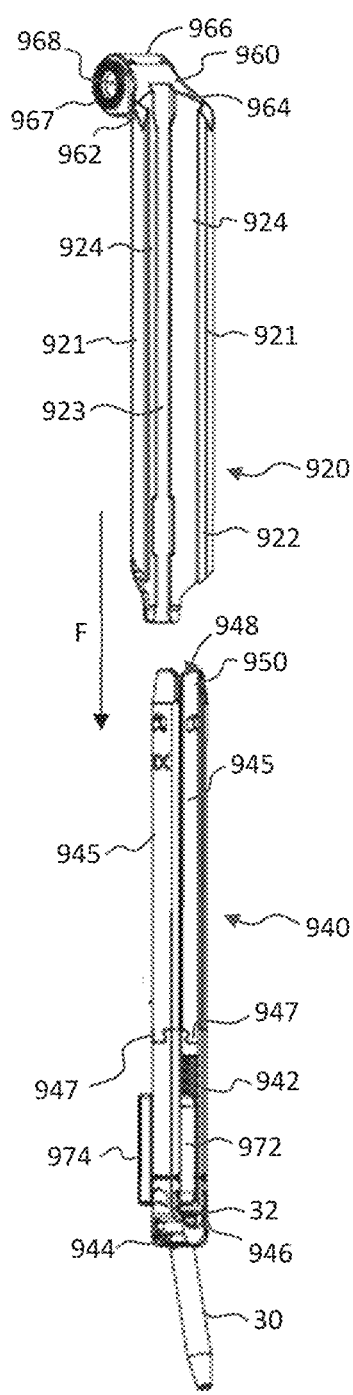
Figure 13C:
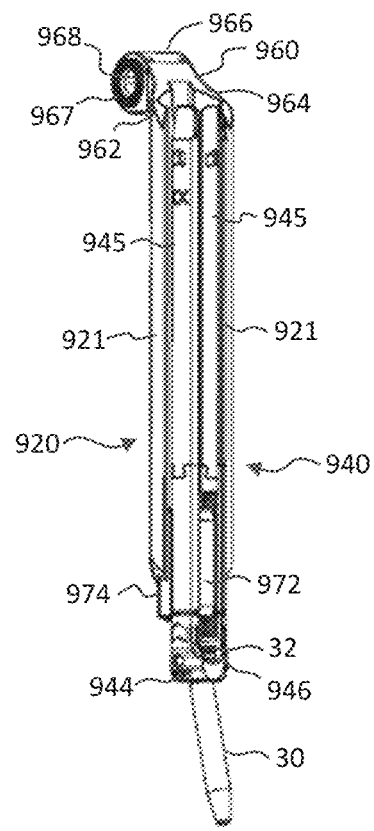

The blade 920 includes a linear blade body 922 with a pair of side rails 921 and a central rail 923 extending the length thereof. A slot 924 extends between the central rail 923 and each respective side rail 921. The central rail 923 is configured to be received in the slot 948 defined by the tulip screw mount 940 when the blade 920 is inserted into the slot 948, as indicated by arrow F in FIG. 13B. In the illustrated embodiment, the central rail 923 is tapered from the free end thereof to the body 922 such that the blade 920 is maintained connected to the tulip screw mount 940. As such, the blade 920 can be translated axially relative to the tulip screw mount 940. As shown in FIG. 13C, the blade 920 contacts the shim 970 and is thereby maintained spaced from the closed end 944 of the tulip screw mount 940.

The proximal end of the blade 920 includes a pivot connection 960. The pivot connection 960 has a body 962 extending from a connection end 964 to a pivot end 966. The connection end 964 is fixed to the proximal end of the blade body 922. The pivot end 966 of the pivot connection 960 includes a transverse through hole 968 configured to receive a post 14 of a retractor system as will be described hereinafter. A plurality of teeth 967 extend about the through hole 968 on each side of the cap body 962.

In an exemplary procedure utilizing the screws 30, tulip screw mounts 940 and blades 920, the surgeons will begin by creating an oblique posterior incision from pedicle to pedicle on one side of the patient and place the MIS screws 30 with the tulip screw mounts 940 into the pedicles. Having the tulip screw mounts 940 already assembled to the pedicle screws 30 allows the connection to be verified prior to insertion into the incision, which will prevent the screw 30 from being placed too deep, and eliminates the need to later attach the tulips in-situ.

With the driver still attached to the screws 30 and acting as a guide, the shims 970 are slid into the slot 948 and then blades 920 are slid down the tulip screw mounts 940, with the central rail 923 extending into the slot 948, to help retract tissue. The blades 920 will be moveable within the tulip screw mounts 940 with the ability to translate up and down with respect thereto. The upward movement is unrestricted and allows the blade 920 to be removed from the tulip screw mounts 940 while a downward movement is restricted by the closed end 944 and bony anatomy. This translation allows the surgeon to place the blade 920 at the ideal height to reduce the most amount of tissue creep.

Figures 13D, 13E:
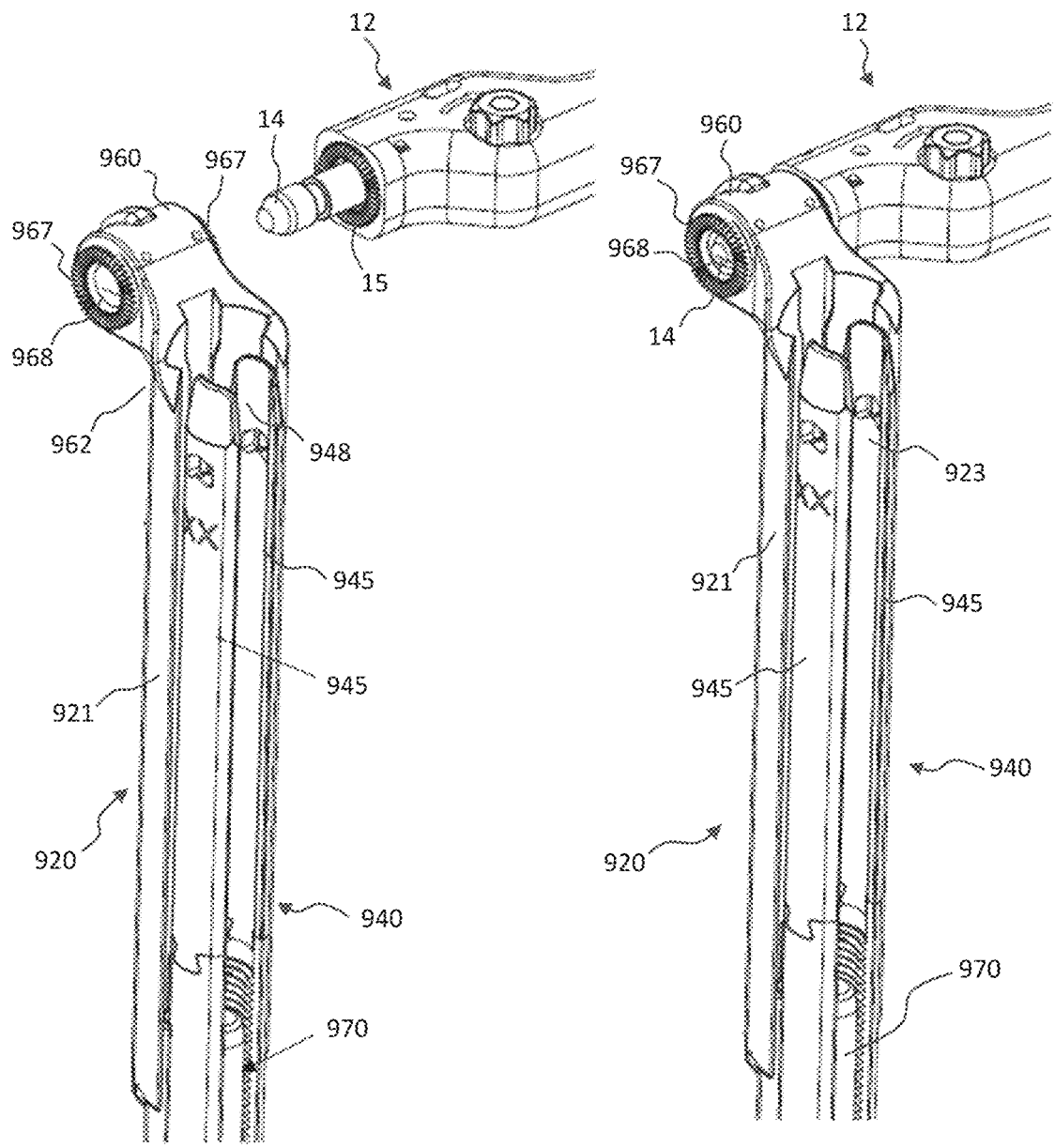

Referring to FIGS. 13D-13ED, the through hole 968 on each pivot connection 960 receives the post 14 of a respective retractor arm 12. Teeth 15 about the post 14 are configured to engage the teeth 967 such that the pivot connection 960, and thereby the blade 920, may be attached to the retractor arm 12 at any desired angle. Once connected to the arms 12, the tulip screw mounts 940, and subsequently the blades 920, will be able to angulate relative to the arms through the use of an angulation mechanism on the retractor arms as well as retract through the use of the retraction mechanism on the retractor frame.

After the interbody cage has been placed, the surgeon may disconnect and remove the shim 970 from the tulip screw mount 940 and blade 920. This will provide space for rod and locking cap insertion while the blades 920 continue to retract soft tissue. Before removing the blade 920 from the incision, a rocking motion may be applied to each blade 920 to break off the extended legs 945 at the breaking features 947.

The systems and methods described with respect to the embodiments in FIG. 11A through FIG. 13E provide secure attachment from the retractor to the screw allow for retraction and distraction of the disc space. Additionally, passive translation between the blade and tulip or blade and shim allows the blade's length to match any patient anatomy and allows the retractor to sit perfectly on each patient's skin level. Furthermore, the tulips are attached to the screw shanks before being inserted which allows for verification of connection, prevents placing the screws too deep, and eliminates the need to attach tulips in-situ at the end of the case.

Components of all of the devices disclosed herein can be made of materials known to those skilled in the art, including metals (e.g., titanium), metal alloys (e.g., stainless steel, cobalt-chromium, and titanium alloys), ceramics, polymers (e.g., polyether ether ketone (PEEK), polyphenylene sulfone (PPSU), polysulfone (PSU), polycarbonate (PC), polyetherimide (PEI), polypropylene (PP), polyacetals, or mixtures or co-polymers thereof), allograft, and/or combinations thereof. In some embodiments, the devices may include radiolucent and/or radiopaque materials. The components can also be machined and/or manufactured using techniques known to those skilled in the art.

Advantageously, the blades, retractor systems, and associated devices described herein can be used with a number of different implants and devices. For example, the retractor systems and devices can be used to provide access to a surgical site such that a device that preserves motion can be provided. In addition, the retractor systems and devices can be used to provide access to a surgical site such that a fusion device, such as a cage or spacer, or standalone device, can be provided. In addition, the retractor systems and devices can be used to provide access to various other devices, including but not limited to rods, screws (e.g., pedicle screws, cortical screws, etc.), plates and various other implants that are used in spine surgery.

As described herein, the specially designed connections between the pedicle screw and retractor blade provide for improved pedicle-based retraction and distraction. The connections create a secure reversible connection between the pedicle screw and the retractor blade. The connections can be made before or during the operation, and if inserted intra-operatively, the blade may be attached to and removed from the screw in a manner to minimize the amount of tissue disruption at the surgical site.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. A retractor blade assembly comprising:
a retractor blade having a proximal end and a distal end configured to retract soft tissue;
a screw mount having an extension portion defining at least one blade mounting assembly and a head portion defining a screw head receiving chamber, the chamber defined by a concave interior wall of the head portion and a moveable retaining member extending from the extension portion with a free end of the retaining member extending within the head portion and defining a concave surface opposed to the concave interior wall; and
a driver including at least one track configured to engage at least one rail on the extension portion of the screw mount the retractor blade configured to engage a second track of the driver and slide down the driver and onto the screw mount such that the distal end of the retractor blade connects to the screw mount.

2. The retractor blade assembly of claim 1, wherein the extension portion includes at least one track configured to slidably engage at least one corresponding rail on the retractor blade.

3. The retractor blade assembly of claim 1, wherein the extension portion includes at least one biased retaining member including a lip configured to engage a corresponding slot in the retractor blade.

4. The retractor blade assembly of claim 3, wherein the slot has an axial length and movement of the lip within the slot over the axial length defines a range of motion of the retractor blade relative to the screw mount.

5. The retractor blade assembly of claim 1, wherein the retaining member is biased radially inward to a retaining position.

6. The retractor blade assembly of claim 5, wherein a locking member is slidable relative to the extension portion between a locked position wherein the retaining member is locked in the retaining position and an unlocked position wherein the retaining member is free to move radially outwardly.

7. The retractor blade assembly of claim 6, wherein the locking member includes an engaging portion which engages the retaining member in the locked position and is aligned with a notch in the retaining member in the unlocked position.

8. The retractor blade assembly of claim 1 wherein the driver includes at least one biased tab configured to engage an opening in the extension portion to releasably retain the driver connected with the screw mount.

9. A retractor blade assembly comprising:
a screw mount including an extension portion and a head portion, the head portion having a concave internal wall and the extension portion including a moveable retaining member with a free end that extends into the head portion such that a concave surface of the retaining member is opposed to the concave internal wall to define a screw head chamber;
a locking mechanism configured to engage the retaining member and preventing the retaining member from moving radially outwardly;
a driver including at least one track configured to engage at least one rail on the extension portion of the screw mount; and
a retractor blade having a proximal portion and a distal portion configured the retractor blade configured to engage with a second track of the driver and to slide down the driver and onto the screw mount such that the distal portion of the retractor blade connects to the screw mount.

* * * * *